United States Patent [19]

Dickinson et al.

[11] Patent Number: 5,116,844

[45] Date of Patent: May 26, 1992

[54] TRIAZOLE ANTIFUNGAL AGENTS

[75] Inventors: Roger P. Dickinson, Dover; Kenneth Richardson, Birchington, both of England

[73] Assignee: Pfizer Inc., New York, N.Y.

[21] Appl. No.: 392,686

[22] Filed: Aug. 11, 1989

[30] Foreign Application Priority Data

Aug. 13, 1988 [GB] United Kingdom ............... 8819308

[51] Int. Cl.$^5$ .................... A01N 43/54; A01N 43/58; A01N 43/40; A01N 43/64
[52] U.S. Cl. ................... 514/269; 514/252; 514/340; 514/383
[58] Field of Search ............. 514/383, 241, 242, 247, 514/256, 338, 269, 252, 340

[56] References Cited

FOREIGN PATENT DOCUMENTS 299684 1/1989 European Pat. Off. .
332387 9/1989 European Pat. Off. .

Primary Examiner—Frederick E. Waddell
Assistant Examiner—K. Weddington
Attorney, Agent, or Firm—Peter C. Richardson; J. Trevor Lumb; James M. McManus

[57] ABSTRACT

The invention provides antifungal agents of the formula:

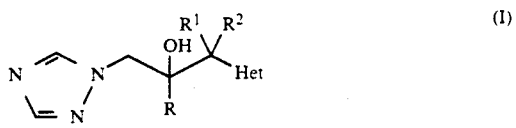

and their pharmaceutically acceptable salts, wherein
R is phenyl optionally substituted by 1 to 3 substituents each independently selected from halo and $CF_3$;
$R^1$ is $C_1$-$C_4$ alkyl;
$R^2$ is H or $C_1$-$C_4$ alkyl; and
"Het", which is attached to the adjacent carbon atom by a ring carbon atom, is selected from pyridinyl, pyridazinyl, pyrimidinyl, pyrazinyl and triazinyl, "Het" being optionally substituted by $C_1$-$C_4$ alkyl, $C_1$-$C_4$ alkoxy, halo, $CF_3$, CN, $NO_2$, $NH_2$, —NH(-$C_1$-$C_4$ alkanoyl) or —$NHCO_2$($C_1$-$C_4$ alkyl).

9 Claims, No Drawings

TRIAZOLE ANTIFUNGAL AGENTS

BACKGROUND OF THE INVENTION

This invention relates to novel triazole derivatives which have antifungal activity and are useful in the treatment of fungal infections in animals, including humans.

SUMMARY OF THE INVENTION

The invention provides antifungal agents of the formula:

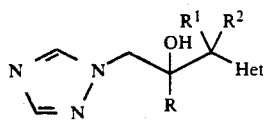

and their pharmaceutically acceptable salts, wherein

R is phenyl optionally substituted by 1 to 3 substituents each independently selected from halo and $CF_3$;

$R^1$ is $C_1$-$C_4$ alkyl;

$R^2$ is H or $C_1$-$C_4$ alkyl; and

"Het", which is attached to the adjacent carbon atom by a ring carbon atom, is selected from pyridinyl, pyridazinyl, pyrimidinyl, pyrazinyl and triazinyl, "Het" being optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —$NHCO_2$($C_1$-$C_4$ alkyl).

In one aspect the invention provides compounds of the formula (I), and their pharmaceutically acceptable salts, wherein "Het" is selected from 2- and 4-pyridinyl, pyridazinyl, 2- and 4-pyrimidinyl, pyrazinyl and triazinyl, "Het" being optionally substituted by $C_1$-$C_4$ alkyl, $C_1$-$C_4$ alkoxy, halo, $CF_3$, CN, $NO_2$, $NH_2$, —NH($C_1$-$C_4$ alkanoyl) or —$NHCO_2$($C_1$-$C_4$ alkyl); and R, $R^1$ and $R^2$ are as previously defined for compounds of the formula (I).

In another aspect, "Het" is pyridinyl, pyridazinyl, pyrimidinyl, pyrazinyl or triazinyl, "Het" being optionally substituted by $C_1$-$C_4$ alkyl, $C_1$-$C_4$ alkoxy, halo, $CF_3$, $NO_2$, $NH_2$ or —NH($C_1$-$C_4$ alkanoyl).

When "Het" is substituted, it is preferably by 1 or 2, most preferably by 1, substituent.

Halo is F, Cl, Br or I.

$C_3$ and $C_4$ alkyl and alkoxy, and $C_4$ alkanoyl groups may be straight or branched chain.

Where R is a substituted phenyl group this includes, for example, 2-fluorophenyl, 2-chlorophenyl, 2-bromophenyl, 2-iodophenyl, 2-trifluoromethylphenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl and 4-bromo-2,5-difluorophenyl.

Preferably, R is a phenyl group substituted by 1 to 3 halo (preferably F or Cl) substituents.

More preferably, R is a phenyl group substituted by 1 or 2 halo (preferably F or Cl) substituents.

Yet more preferably, R is 2,4-difluorophenyl, 2,4-dichlorophenyl, 2-fluorophenyl or 2-chlorophenyl.

Most preferably, R is 2,4-difluorophenyl.

Preferably, $R^1$ is methyl and $R^2$ is H or methyl.

Most preferably, $R^1$ is methyl and $R^2$ is H.

Preferably, "Het" is selected from pyridinyl, pyridazinyl, pyrimidinyl, pyrazinyl and triazinyl, all optionally substituted by 1 or 2 substituents each independently selected from $C_1$-$C_4$ alkyl, $C_1$-$C_4$ alkoxy, halo, $CF_3$, CN, $NO_2$, $NH_2$, —NH($C_1$-$C_4$ alkanoyl) and —$NHCO_2$($C_1$-$C_4$ alkyl).

More preferably, "Het" is selected from pyridinyl, pyridazinyl, pyrimidinyl and pyrazinyl, all optionally substituted by 1 or 2 substituents each independently selected from $C_1$-$C_4$ alkyl, $C_1$-$C_4$ alkoxy, halo, $CF_3$, CN, $NH_2$, —NH($C_1$-$C_4$ alkanoyl) and —$NHCO_2$($C_1$-$C_4$ alkyl).

Yet more preferably, "Het" is selected from pyridinyl, pyridazinyl, pyrimidinyl and pyrazinyl, all optionally substituted by one CN, $NH_2$ or —$NHCO_2$($C_1$-$C_4$ alkyl) substituent.

The preferred pyridinyl and pyrimidinyl groups are 2- and 4-pyridinyl and 2- and 4-pyrimidinyl, all optionally substituted as defined above.

More preferably still, "Het" is selected from pyridinyl (preferably 2- and 4-pyridinyl), pyridazinyl, 2- and 4-pyrimidinyl and pyrazinyl, all optionally substituted by one CN, $NH_2$ or —$NHCO_2$($C_1$-$C_4$ alkyl) substituent.

Most preferably, "Het" is 2-pyridinyl, 4-pyridinyl, or 4-pyrimidinyl.

The pharmaceutically acceptable salts of the compounds of the formula (I) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts.

Particularly preferred individual compounds are 2-(2,4-difluorophenyl)-3-(pyridin-2-yl)-1-(1H-1,2,4-triazol-1-yl)butan-2-ol, 2-(2,4-difluorophenyl)-3-(pyridin-4-yl)-1-(1H-1,2,4-triazol-1-yl)butan-2-ol and 2-(2,4-difluorophenyl)-3-(pyrimidin-4-yl)-1-(1H-1,2,4-triazol-1-yl)butan-2-ol;

and pharmaceutically acceptable salts thereof.

DETAILED DESCRIPTION OF THE INVENTION

The compounds of the formula (I) provided by the invention may be prepared by the following methods:

(1) The compounds of the formula:

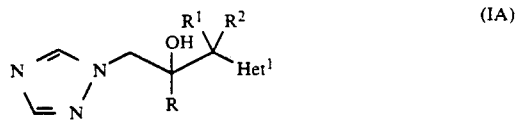

wherein R, $R^1$ and $R^2$ are as defined for formula (I) and "$Het^1$" is a pyridinyl, pyridazinyl, pyrimidinyl, pyrazinyl or triazinyl group, "$Het^1$" being optionally substituted by $C_1$-$C_4$ alkyl, $C_1$-$C_4$ alkoxy, halo, $CF_3$, CN or $NO_2$, may be prepared as follows:

METHOD (A)

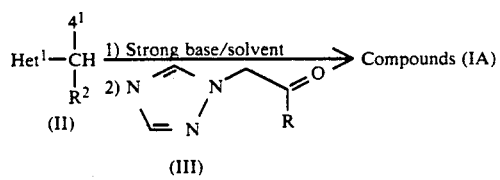

wherein R, $R^1$, $R^2$ and "$Het^1$" are as defined for formula (IA).

In a typical procedure, the compound of the formula (II) is deprotonated by the addition of approximately one equivalent of a suitable strong base, e.g. lithium diisopropylamide, and the resulting salt (preferably the lithium, sodium or potassium salt) is reacted in situ with the ketone of the formula (III). The reaction is typically carried out at from $-80°$ to $-50°$ C., preferably at about $-70°$ C., in a suitable organic solvent, e.g. tetrahydrofuran or diethyl ether, and under an inert atmosphere, e.g. nitrogen or argon.

The starting materials of the formula (II) are known compounds or may be prepared by conventional procedures (see Examples section). The starting materials of the formula (III) are known compounds (see e.g. EP-A-44605, EP-A-69442 or GB-A-1464224) or may be prepared by analogous methods; or

METHOD (B)

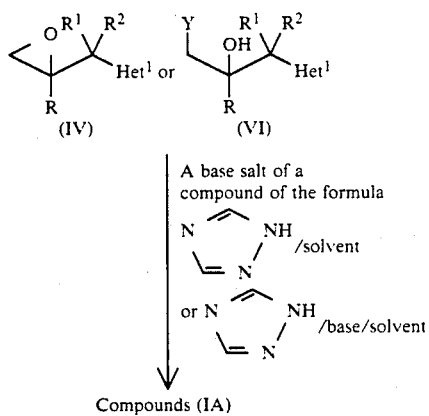

wherein R, $R^1$, $R^2$ and "$Het^1$" are as defined for formula (IA), and Y is a leaving group, e.g. chloro, bromo or $C_1$-$C_4$ alkanesulphonyloxy (such as methanesulphonyloxy). Examples of suitable base salts of 1H-1,2,4-triazole are alkali metal (preferably sodium) and tetraalkylammonium (preferably tetra-n-butylammonium [see U.S. Pat. No. 4259505]) salts.

The reaction is preferably carried out using the epoxide (IV) as the starting material. If a compound of the formula (VI) is used in this process, it is probable that the reaction mechanism dictates, at least in part, that an epoxide of the formula (IV) is formed in situ under the reaction conditions. The process is therefore, in this respect, similar to that utilising the epoxide (IV) as the starting material.

When a base salt of 1H-1,2,4-triazole is used, the reaction is typically carried out at from room temperature to 100° C., preferably at about 60° C. when using the sodium salt of 1H-1,2,4-triazole, and preferably at room temperature when using the corresponding tetra-n-butylammonium salt, in a suitable organic solvent, e.g. N,N-dimethylformamide or tetrahydrofuran.

Alternatively, the reaction may be carried out using 1H-1,2,4-triazole in the presence of an additional base, e.g. $Na_2CO_3$ or $K_2CO_3$, preferably at from 50° to 100° C. in a suitable organic solvent, e.g. N,N-dimethylformamide or methanol.

The intermediates of the formula (IV) and (VI) may be prepared by conventional techniques, e.g. as described in the Examples section, and as summarised by the following Schemes A and B:

SCHEME A

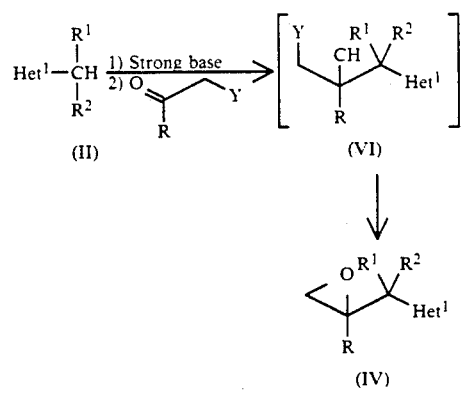

wherein R, $R^1$, $R^2$ and "$Het^1$" are as defined for formula (IA), and Y is a leaving group, preferably Cl or Br.

In a typical procedure, a compound of the formula (II) is deprotonated by the addition of approximately one equivalent of a suitable strong base, e.g. lithium diisopropylamide, and the resulting organometallic intermediate is reacted in situ with the compound of the formula (V). The reaction is typically carried out at from $-80°$ to $-50°$ C., preferably at about $-70°$ C., in a suitable organic solvent, e.g. tetrahydrofuran or diethyl ether, and under an inert atmosphere, e.g. nitrogen or argon. The intermediate compound (VI) need not be isolated, and is generally cyclised in situ after a period of stirring at a higher temperature (e.g. room temperature), to provide the oxirane of the formula (IV).

The compounds of the formula (VI) when Y is chloro or bromo may also be prepared by reacting the epoxide (IV) with the appropriate hydrogen halide under anhydrous conditions; or

SCHEME B

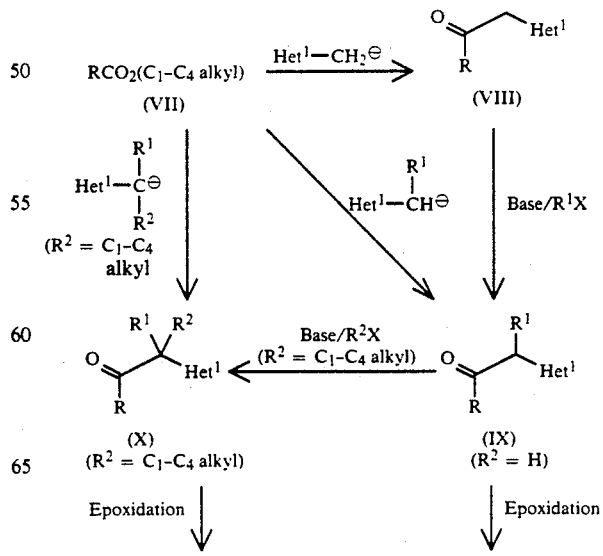

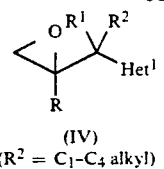
(IV)
(R² = C₁-C₄ alkyl)

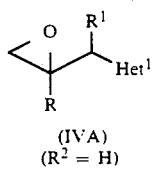
(IVA)
(R² = H)

wherein R, R¹, R² and "Het¹" are as defined for formula (IA), and X is a suitable leaving group, e.g. Cl, Br, I or methanesulphonyloxy.

In a typical procedure, the compounds of the formula (VIII), (IX) and (X) are prepared directly from an ester of the formula (VII) by reaction with an organometallic intermediate derived, as appropriate, by deprotonation of a compound of the formula Het¹—CH₃ or Het¹—CHR¹R² (compound II), wherein Het¹, R¹ and R² are as defined for formula (IA), with approximately one equivalent of a suitable strong base, e.g. lithium diisopropylamide. The reaction is typically carried out at from −80° to −50° C., preferably at about −70° C., in a suitable organic solvent, e.g. tetrahydrofuran or diethyl ether, and under an inert atmosphere, e.g. nitrogen or argon.

Although not shown in Scheme B, the compounds of the formula (VIII) or (IX) when "Het¹" is 3-pyridinyl or 5-pyrimidinyl and R and R¹ are as defined for formula (IA), may also be conveniently prepared from an Alternatively, the compounds of the formula (IX) and (X) may be prepared by reacting, respectively, a compound of the formula (VIII) or (IX) with approximately one equivalent of a suitable base, e.g. sodium hydride, followed by alkylation of the resultant carbanion in situ with a suitable alkylating agent. The reaction is typically carried out at from 0° C. to room temperature in a suitable organic solvent, e.g. N,N-dimethylformamide.

Preferably, alkylation of a compound of the formula (VIII) or (IX) is performed under phase transfer conditions, e.g. using NaOH/[CH₃(CH₂)₃]₄N⊕⊖HSO₄/H₂O/CHCl₃/(C₁-C₄alkyl)X (wherein X is preferably iodo), at from 0° C. to room temperature, and typically at room temperature.

Epoxidation of the ketones of the formula (IX) or (X) is performed using conventional methods, e.g. using dimethyloxosulphonium methylide (see e.g. J. A. C. S. [1965], 87, 1353) or chloromethyllithium (see e.g. Tet. Lett. [1986], 795). (2) The compounds of the formula (I) in which "Het" is monosubstituted with a cyano group positioned on a ring carbon atom which is adjacent to a ring nitrogen atom, wherein "Het" is pyridinyl, pyridazinyl, pyrimidinyl, pyrazinyl or triazinyl. and R, R¹ and R² are as defined for the formula (I), are most conveniently prepared from unsubstituted "Het" precursors by a method as shown in Scheme C:

SCHEME C

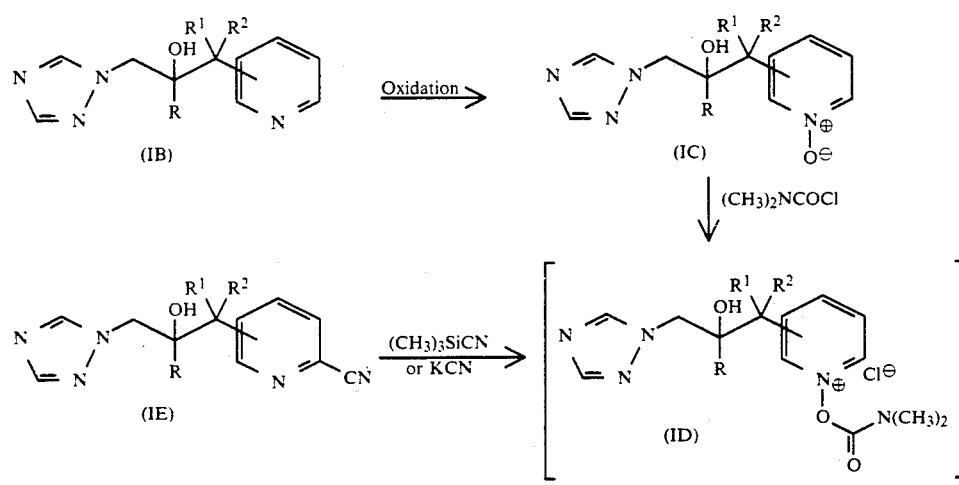

ester of the formula (VII) by reaction with an organometallic derivative derived by deprotonation of a compound of the formula:

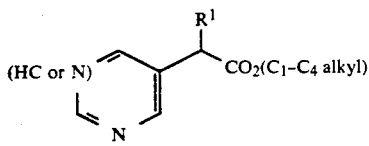

wherein R¹ is C₁-C₄ alkyl, in situ, using similar methodology to that described in the previous paragraph. The intermediate β-ketoester obtained after work-up is then subjected to hydrolysis/decarboxylation by treatment with a suitable strong mineral acid, e.g. concentrated hydrochloric acid, preferably under reflux conditions, to provide the compound of the formula (VIII) or (IX), as appropriate.

The procedure is illustrated for a compound of the formula (I) when "Het" is pyridinyl, although similar methodology applies for all definitions of "Het" given previously in this method, with the proviso that "Het" must have at least one unsubstituted ring carbon atom which is adjacent to the ring nitrogen atom which is N-oxidised.

"Het" is preferably pyridinyl or pyrimidinyl in this method.

Depending on the specific "Het" group used and/or the position of attachment thereof, the possibility of the formation of two regioisomers exists in this process. Such regioisomers, where formed, may be separated by conventional techniques, e.g. by column chromatography.

In a typical procedure, a compound of the formula (IB) is oxidised to provide an N-oxide of the formula (IC). The reaction is preferably carried out using 3- chloroperoxybenzoic acid in a suitable solvent, e.g. dichloromethane, at from 0° C. to the reflux temperature thereof, and preferably at room temperature. The oxidation may alternatively be carried out using hydrogen peroxide in a suitable $C_1$-$C_4$ alkanoic acid, e.g. acetic acid.

Treatment of the N-oxide (IC) with N,N-dimethylcarbamoyl chloride, followed by either trimethylsilyl cyanide or potassium cyanide according to the method of W. K. Fife (J. Org. Chem., 48, 1375 [1983] and, et al, Heterocycles, 22, 1121 [1984]) provided the cyano-substituted compound (IE). The reaction is preferably carried out using N,N-dimethylcarbamoyl chloride and trimethylsilyl cyanide in dichloromethane at room temperature, and may also be carried out stepwise, i.e. by initial addition of N,N-dimethylcarbamoyl chloride to the N-oxide, followed by a period of stirring before trimethylsilyl cyanide is added.

(3) Some of the compounds of the formula (I) may be prepared from other compounds of the formula (I) by "functional group interconversion", as follows:

(a) A cyano group on "Het" may be converted to a —NHCO$_2$($C_1$-$C_4$ alkyl) substituent by the following stepwise procedure:

(i) The cyano compound is initially treated with a $C_1$-$C_4$ alkanol, e.g. methanol, under acidic conditions, and typically under reflux, to convert the cyano group to a —CO$_2$($C_1$-$C_4$ alkyl) group. Alternatively, hydrolysis of the cyano compound under conventional acidic or basic conditions provides the corresponding carboxylic acid, which may then be esterified using a $C_1$-$C_4$ alkanol under acidic conditions.

(ii) The ester group is converted to a —CONHNH$_2$ group by treatment of the ester with hydrazine (preferably hydrazine hydrate) in a suitable organic solvent, e.g. a $C_1$-$C_4$ alkanol such as isopropanol, at from room temperature to, and preferably at, the reflux temperature thereof.

(iii) Finally the —CONHNH$_2$ group is converted to the required —NHCO$_2$($C_1$-$C_4$ alkyl) group under the conditions of the Curtius rearrangement reaction, i.e. by treatment of the carboxylic acid hydrazide with nitrous acid, preferably at about 0° C., followed by work-up of the intermediate azide obtained and treatment thereof with a $C_1$-$C_4$ alkanol, preferably under reflux conditions;

(b) A —NHCO$_2$($C_1$-$C_4$ alkyl) substituent on "Het" may be converted to an amino substituent by hydrolysis under basic conditions, e.g. using an aqueous solution of sodium or potassium hydroxide in a $C_1$-$C_4$ alkanol (e.g. ethanol or isopropanol) under reflux conditions;

(c) A nitro substituent on "Het" may be reduced to an amino substituent by conventional procedures. Preferably, the reduction is carried out by catalytic hydrogenation using a suitable catalyst, e.g. palladium/charcoal, and in a suitable organic solvent, e.g. ethanol. The reduction may also be carried out using stannous chloride at up to, and preferably at, the reflux temperature in a suitable organic solvent, e.g. ethanol;

(d) An amino substituent on "Het" may be converted to a substituent of the formula —NH($C_2$-$C_4$ alkanoyl) by acylation with either a $C_2$-$C_4$ alkanoyl halide or with an acid anhydride of the formula ($C_2$-$C_4$ alkanoyl)$_2$O. When an alkanoyl halide is employed the reaction is typically carried out from 0° C. to room temperature in a suitable organic solvent, e.g. methylene chloride, and in the presence of a suitable acid acceptor, e.g. triethylamine or pyridine. The reaction may also be carried out using pyridine as both the solvent and the acid acceptor. When an acid anhydride is employed, the reaction is typically carried out at up to the reflux temperature, preferably at 100° C., in a suitably compatible organic solvent, e.g. a $C_2$-$C_4$ alkanoic acid;

(e) An amino substituent on "Het" may be converted to a substituent of the formula —NHCHO using conventional techniques, e.g. by formylation using acetic-formic anhydride; or (f) An amino substituent on "Het" may be converted to a halo substituent by initial reaction with sodium nitrite in a suitably compatible aqueous mineral acid, e.g. aqueous hydrochloric or sulphuric acid, preferably at about 0° C., to form a diazonium salt intermediate. Further treatment with (i) cuprous chloride or bromide, as appropriate, introduces a chloro or bromo substituent into "Het";

(ii) potassium iodide introduces an iodo substituent into "Het"; or (iii) fluoboric acid causes precipitation of the diazonium fluoborate, which may be filtered off, dried and thermally decomposed to introduce a fluoro substituent into "Het".

All of the above reactions are conventional and appropriate reagents and reaction conditions for their performance and procedures for isolating the desired products will be well known to those skilled in the art, in accordance with literature precedents and by reference to the Examples hereto.

Where $R^1$ is identical to $R^2$, the compounds of the formula (I) contain at least one chiral centre and therefore exist as a pair of enantiomers or as diastereoisomeric pairs of enantiomers. Where $R^1$ and $R^2$ are different, the compounds of the formula (I) contain at least two chiral centres (*) and therefore exist as at least two diastereoisomeric pairs of enantiomers, i.e.

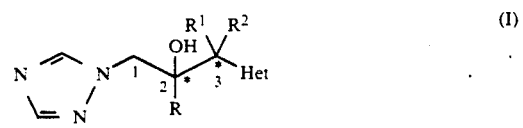

The invention includes both the individual stereoisomers of the compounds of the formula (I) together with mixtures thereof. Resolution may be achieved by conventional techniques, e.g. by fractional crystallisation, chromatography or H.P.L.C. of the stereoisomeric mixture of the parent compound or of a suitable salt or derivative thereof. Most preferably, the individual diastereoisomers or the resolved diastereoisomeric pairs of enantiomers of the compounds of the formula (I) containing two chiral centres are prepared from resolved intermediates as illustrated in the following Examples section.

The preferred compounds of the formula (I) when $R^2$ is H have the (2R,3S) configuration, i.e.

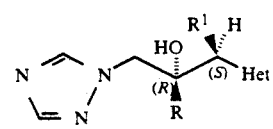

Particularly preferred individual diastereoisomers are
(2R,3S)-2-(2,4-difluorophenyl)-3-(pyridin-2-yl)-1-(1H-1,2,4-triazol-1-yl)butan-2-ol,
(2R,3S)-2-(2,4-difluorophenyl)-3-(pyridin-4-yl)-1-(1H-1,2,4-triazol-1-yl)butan-2-ol and
(2R,3S)-2-(2,4-difluorophenyl)-3-(pyrimidin-4-yl)-1-(1H-1,2,4-triazol-1-yl)butan-2-ol;
and pharmaceutically acceptable salts thereof.

Pharmaceutically acceptable acid-addition salts are readily prepared by mixing solutions containing equimolar amounts of the free base and the desired acid. The salt generally precipitates from solution and is collected by filtration, or is recovered by evaporation of the solvent.

The compounds of the formula (I) and their salts are anti-fungal agents, useful in the curative or prophylactic treatment of fungal infections in animals, including humans. For example, they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Aspergillus fumigatus,* Coccidioides, Paracoccidioides, Histoplasma or Blastomyces.

The compounds of the present invention have been found to have unexpectedly good activity against the clinically-important Aspergillus sp. fungi.

The in vitro evaluation of the antifungal activity of the compounds can be performed by determining the minimum inhibitory concentration (m.i.c.), which is the concentration of the test compounds, in a suitable medium, at which growth of the particular micro-organism fails to occur. In practice, a series of agar plates, each having the test compound incorporated at a particular concentration is inoculated with a standard culture of, for example, *Candida albicans*, and each plate is then incubated for 48 hours at 37° C. The plates are then examined for the presence or absence of growth of the fungus and the appropriate m.i.c. value is noted. Other micro-organisms used in such tests can include *Aspergillus fumigatus*, Trichophyton spp, Microsporum spp, *Epidermophyton floccosum, Coccidioides immitis* and *Torulopsis glabrata*.

The in vivo evaluation of the compounds can be carried out at a series of dose levels by intraperitoneal or intravenous injection, or by oral administration, to mice which are inoculated with, e.g., a strain of *Candida albicans* or *Aspergillus fumigatus*. Activity is based on the survival of a treated group of mice after the death of an untreated group of mice. The dose level at which the compound provides 50% protection against the lethal effect of the infection ($PD_{50}$) is noted.

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts will be from 0.01 to 20 mg/kg (in single or divided doses) when administered by either the oral or parenteral route. Thus tablets or capsules of the compounds will contain from 5 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

It has also been found that the compounds of the formula (I) when $R^1$ and $R^2$ are H and R and "Het" are as defined for formula (I), have antifungal activity in animals, and that they are particularly active against Aspergillus sp. fungi.

Thus, the invention further provides a pharmaceutical composition comprising a compound of the formula (I), or a pharmaceutically acceptable salt thereof, together with a pharmaceutically acceptable diluent or carrier.

The invention yet further provides a compound of the formula (I), or a pharmaceutically acceptable salt or composition thereof, for use as a medicament, in particular as an antifungal agent.

The invention also provides the use of a compound of the formula (I), or of a pharmaceutically acceptable salt or composition thereof, for the manufacture of an antifungal agent.

The invention yet further provides a method of treating an animal (including a human being) to cure or prevent a fungal infection, which comprises treating said animal with an effective amount of a compound of the formula (I), or with, as appropriate, a pharmaceutically acceptable salt or composition thereof.

The invention also includes any novel intermediates disclosed herein, such as those of the formulae (IV), (VI), (IX) and (X).

The following Examples, in which all the temperatures are in °C., illustrate the invention:

EXAMPLE 1

2-(2,4-Difluorophenyl)-3-(pyridin-2-yl)-1-(1H-1,2,4-triazol-1-yl)butan-2-ol

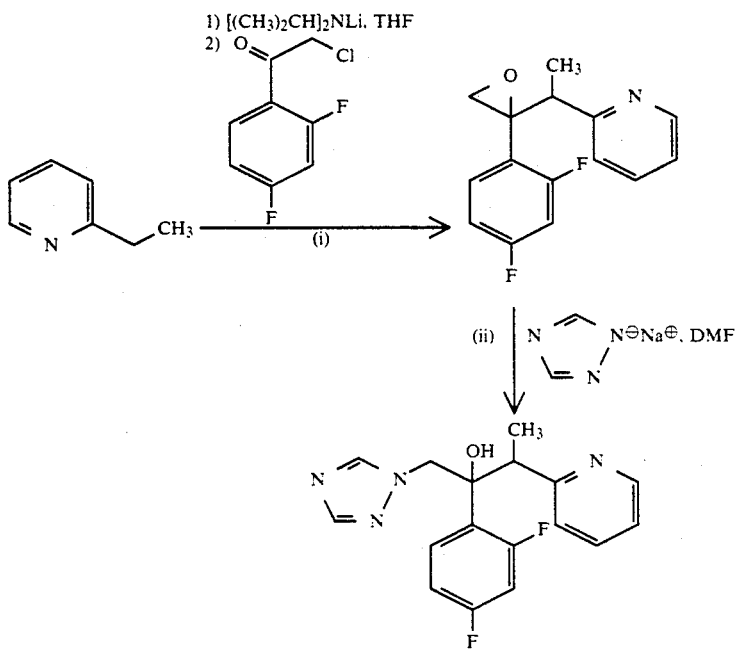

(i)

2-(2,4-Difluorophenyl)-2-(1-[pyridin-2-yl]ethyl)oxirane n-Butyllithium (19.7 ml of a 1.6M solution in hexane) was added to a stirred solution of diisopropylamine (3.18 g) in dry tetrahydrofuran (50 ml) at −70° under an atmosphere of dry nitrogen. The solution was stirred at −70° for 0.17 hour, followed by 0.17 hour at 0° and then re-cooled to −70°. 2-Ethylpyridine (3.37 g) was added over 0.08 hour, the red solution resulting was stirred at −70° for 0.33 hour and then added via a syringe to a stirred solution of 2-chloro-2',4'-difluoroacetophenone (5.00 g) in dry tetrahydrofuran (50 ml) at −70°. The solution was stirred at −70° for 3 hours and then at room temperature for 18 hours. Water (4 ml) was added and the solution was evaporated. The residual oil was partitioned between water (80 ml) and dichloromethane (100 ml). The organic layer was separated, washed with water (80 ml) and then extracted with 2N hydrochloric acid (2×80 ml). The combined acidic extracts were basified to pH 12 with 2N sodium hydroxide solution and extracted with dichloromethane (3×75 ml). The combined organic layers were dried (Na₂SO₄), evaporated, and the residue was chromatographed on silica gel. Elution with ethyl acetate gave, after combination and evaporation of appropriate fractions, the title compound (2.25 g) as a yellow oil which was used directly in the next stage.

(ii)

2-(2,4-Difluorophenyl)-3-(pyridin-2-yl)-1-(1H-1,2,4-triazol-1-yl)butan-2-ol

A mixture of the product of part (i) (2.20 g) and 1H-1,2,4-triazole sodium salt (1.53 g) in N,N-dimethylformamide (15 ml) was heated at 60° with stirring for 18 hours and then evaporated. Water (50 ml) was added and the mixture was extracted with ethyl acetate (3×50 ml). The combined extracts were dried (Na₂SO₄), evaporated and the residue was chromatographed on silica gel. Elution with ethyl acetate first gave, after combination and evaporation of appropriate fractions, the title compound, diastereoisomeric pair A, (0.93 g), m.p. 146°-148° (from ether).

Analysis %: Found: C,61.69; H,4.73; N,16.88; $C_{17}H_{16}F_2N_4O$ requires: C,61.81; H,4.88; N,16.96.

Further elution with ethyl acetate gave, after combination and evaporation of appropriate fractions, the title compound, diastereoisomeric pair B, (0.63 g), m.p. 151°-152° (from ether).

Analysis %: Found: C,61.68; H,4.79; N,17.01; $C_{17}H_{16}F_2N_4O$ requires: C,61.81; H,4.88; N,16.96.

EXAMPLE 2

2-(2,4-Difluorophenyl)-3-(pyridin-4-yl)-1-(1H-1,2,4-triazol-1-yl)butan-2-ol

Method A

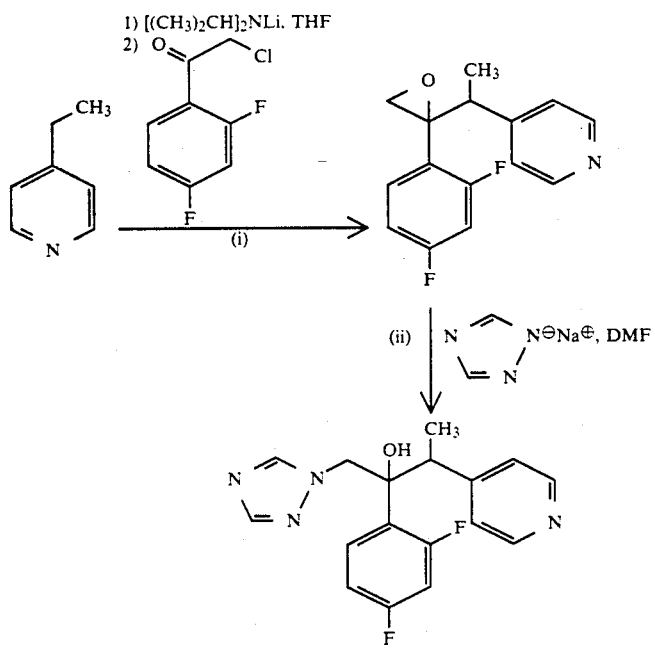

(i)
2-(2,4-Difluorophenyl)-2-(1-[pyridin-4-yl]ethyl)oxirane

Lithium diisopropylamide was prepared by addition of n-butyllithium (19.7 ml of a 1.6M solution in hexane) to a solution of diisopropylamine (3.18 g) in dry tetrahydrofuran (50 ml), and the resulting solution was treated successively with 4-ethylpyridine (3.37 g) and a solution of 2-chloro-2',4'-difluoroacetophenone (5.00 g) in dry tetrahydrofuran (50 ml) according to the method of Example 1(i). Work-up of the reaction mixture as before afforded the title compound (1.05 g) as a yellow oil which was used directly in the next stage.

(ii)
2-(2,4-Difluorophenyl)-3-(pyridin-4-yl)-1-(1H-1,2,4-triazol-1-yl)butan-2-ol Treatment of the product of part (i) (1.02 g) with 1H-1,2,4-triazole sodium salt (0.71 g) in N,N-dimethylformamide (10 ml) by the method of Example 1(ii), followed by chromatography of the crude product on silica gel using dichloromethane/methanol (97:3) as eluant, first gave, after combination and evaporation of appropriate fractions, the title compound, diastereoisomeric pair A, (0.22 g), m.p. 161°-163° (from ether).

Analysis %: Found: C,61.87; H,4.89; N,16.96; $C_{17}H_{16}F_2N_4O$ requires: C,61.81; H,4.88; N,16.96.

Further elution with dichloromethane/methanol (97:3) gave, after combination and evaporation of appropriate fractions, the title compound, diastereoisomeric pair B, (0.35 g), m.p. 156°-158° (from ether).

Analysis %: Found: C,61.79; H,4.86; N,17.31; $C_{17}H_{16}F_2N_4O$ requires: C,61.81; H,4.88; N,16.96.

Method B

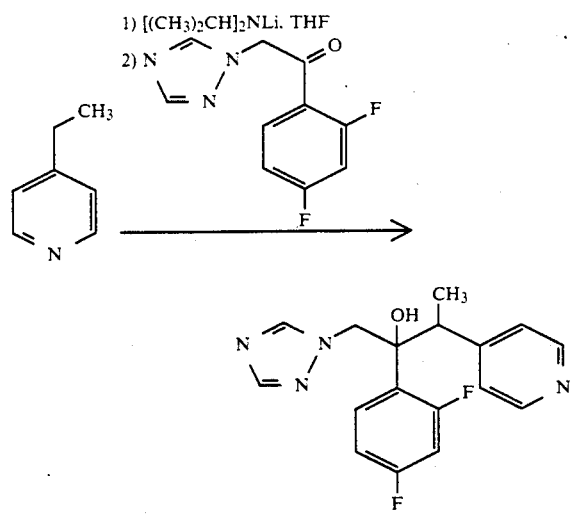

2-(2,4-Difluorophenyl)-3-(pyridin-4-yl)-1-(1H-1,2,4-triazol-1-yl)butan-2-ol

A solution of lithium diisopropylamide was prepared as described in Example 1(i) from diisopropylamine (40.4 g) and n-butyllithium (160 ml of a 2.5M solution in hexane) in dry tetrahydrofuran (800 ml) under an atmosphere of dry nitrogen. To this solution at −70° was added 4-ethylpyridine (42.8 g), dropwise with stirring over 0.17 hour. The solution was stirred at −70° for 0.33 hour and then a solution of 1-(2,4-difluorophenyl)-2-(1H-1,2,4-triazol-1-yl)ethanone (89.2 g) in dry tetrahydrofuran (350 ml) was added over 0.33 hour. The solution was stirred at −70° for a further 0.75 hour and then acetic acid (40 ml) was added dropwise. The solution was allowed to reach room temperature and was diluted with water. The mixture was extracted three times with ether and the combined extracts were washed with water. The aqueous washings were extracted once with ethyl acetate and the organic extracts were combined, dried (Na₂SO₄) and evaporated. The residue was dissolved in boiling dichloromethane, an equal volume of ether was added and then the solution was allowed to cool. The precipitated solid was filtered off to give recovered ketone starting material (17.5 g). The filtrate was evaporated and the residue was chromatographed on silica gel. Initial elution with ethyl acetate/hexane (1:1) gave further recovered ketone starting material. Further elution with ethyl acetate gave fractions containing the title compound, diastereoisomeric pair A (not treated further). The solvent was then changed to ethyl acetate/methanol (19:1) and elution was continued until pure fractions containing the title compound, diastereoisomeric pair B, were obtained. These fractions were combined, evaporated and the residue was crystallised from dichloromethane/ether to give the title compound, diastereoisomeric pair B, (20.5 g), m.p. 155°–157° (N.M.R. [300 MHz] spectrum identical with that obtained for a sample of diastereoisomeric pair B prepared as described in Method A, part (ii)).

Recrystallisation from acetonitrile gave a polymorph, m.p. 165.5°–166.5°.

Analysis %: Found: C,61.69; H,4.85; N,16.85; $C_{17}H_{16}F_2N_4O$ requires: C,61.81; H,4.88; N,16.96.

X-Ray crystallography assigned the stereochemistry of diastereoisomeric pair B as being a racemic mixture of the (2R,3S) and (2S,3R) diastereoisomers.

EXAMPLE 3

2-(2,4-Difluorophenyl)-3-(pyrimidin-4-yl)-1-(1H-1,2,4-triazol-1-yl)butan-2-ol

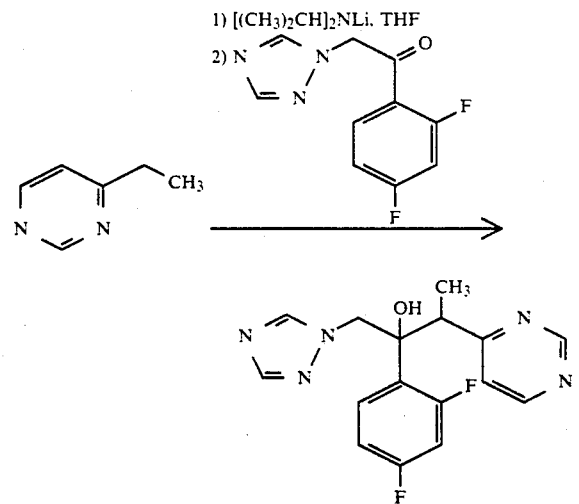

n-Butyllithium (4.0 ml of a 2.5M solution in hexane) was added to a stirred solution of diisopropylamine (1.01 g) in dry tetrahydrofuran (30 ml) at −70° under an atmosphere of dry nitrogen. The solution was stirred at −70° for 0.17 hour, followed by 0.17 hour at 0° and then re-cooled to −70°. 4-Ethylpyrimidine (1.08 g) was added and the solution was stirred at −70° for 0.75 hour. A solution of 1-(2,4-difluorophenyl)-2-(1H-1,2,4-triazol-1-yl)ethanone (2.23 g) in dry tetrahydrofuran (30 ml) was added over 0.17 hour. The solution was stirred at −70° for 1 hour and then acetic acid (1 ml) was added. The solution was allowed to reach room temperature and was then diluted with water. The mixture was extracted three times with ethyl acetate and the combined extracts were washed with water then dried (Na₂SO₄). The solvent was evaporated and the residue was chromatographed on silica gel. Initial elution with ethyl acetate/hexane (3:2) gave recovered ketone starting material. Further elution with ethyl acetate gave, after combination and evaporation of appropriate fractions, the title compound, diastereoisomeric pair A, (0.305 g), m.p. 114°–115.5° (from ether/hexane).

Analysis %: Found: C,57.76; H,4.45; N,21.26; $C_{16}H_{15}F_2N_5O$ requires: C,58.00; H,4.56; N,21.14.

Further elution with ethyl acetate/methanol (19:1) gave, after combination and evaporation of appropriate fractions, the title compound, diastereoisomeric pair B, (0.215 g), m.p. 104°–105° (from ether/hexane).

Analysis %: Found: C,57.63; H,4.44; N,21.36; $C_{16}H_{15}F_2N_5O$ requires: C,58.00; H,4.56; N,21.14.

EXAMPLES 4-7

The following tabulated Examples of the general formula:

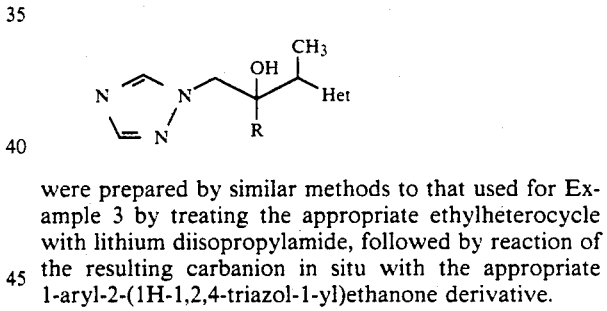

were prepared by similar methods to that used for Example 3 by treating the appropriate ethylheterocycle with lithium diisopropylamide, followed by reaction of the resulting carbanion in situ with the appropriate 1-aryl-2-(1H-1,2,4-triazol-1-yl)ethanone derivative.

| Example No. | R | Het | Diastereoisomeric pair[1] | m.p. (°C.) | Analysis % |
|---|---|---|---|---|---|
| 4 | ![2-F-phenyl] | ![pyrimidinyl] | A | 120–121 | Found: C, 61.34; H, 5.11; N, 22.36; $C_{16}H_{16}FN_5O$ requires: C, 61.44; H, 5.22; N, 22.02. |
|  |  |  | B | 101–103 | Found: C, 60.62; H, 5.28; N, 21.73; $C_{16}H_{16}FN_5O$ requires: C, 61.44; H, 5.22; N, 22.02. |

-continued

| Example No. | R | Het | Diastereoisomeric pair[1] | m.p. (°C.) | Analysis % |
|---|---|---|---|---|---|
| 5 | 2-chlorophenyl | pyridin-2-yl | A | 127–128.5 | Found: C, 61.70; H, 5.25; N, 17.02; $C_{17}H_{17}ClN_4O$ requires: C, 62.10; H, 5.21; N, 17.04; |
|   |   |   | B | 128–129.5 | Found: C, 62.40; H, 5.28; N, 16.99; $C_{17}H_{17}ClN_4O$ requires: C, 62.10; H, 5.21; N, 17.04. |
| 6 | 2-chlorophenyl | pyridin-4-yl | B[2] | 151–152.5 | Found: C, 61.94; H, 5.17; N, 17.18; $C_{17}H_{17}ClN_4O$ requires: C, 62.10; H, 5.21; N, 17.04. |
| 7 | 2-chlorophenyl | pyrimidin-4-yl | A | 130–131.5 | Found: C, 58.58; H, 4.99; N, 21.00; $C_{16}H_{16}ClN_5O$ requires: C, 58.27; H, 4.89; N, 21.24. |
|   |   |   | B | 135.5–136.5 | Found: C, 58.25; H, 4.93; N, 21.32; $C_{16}H_{16}ClN_5O$ requires: C, 58.27; H, 4.89; N, 21.24. |

[1]Diastereoisomeric pair B is more polar on T.L.C. (silica gel) than diastereoisomeric pair A in all the tabulated Examples.
[2]Less polar diastereoisomeric pair A not isolated in this case.

EXAMPLE 8

2-(2,4-Difluorophenyl)-3-methyl-3-(pyrimidin-4-yl)-1-(1H-1,2,4-triazol-1-yl)butan-2-ol

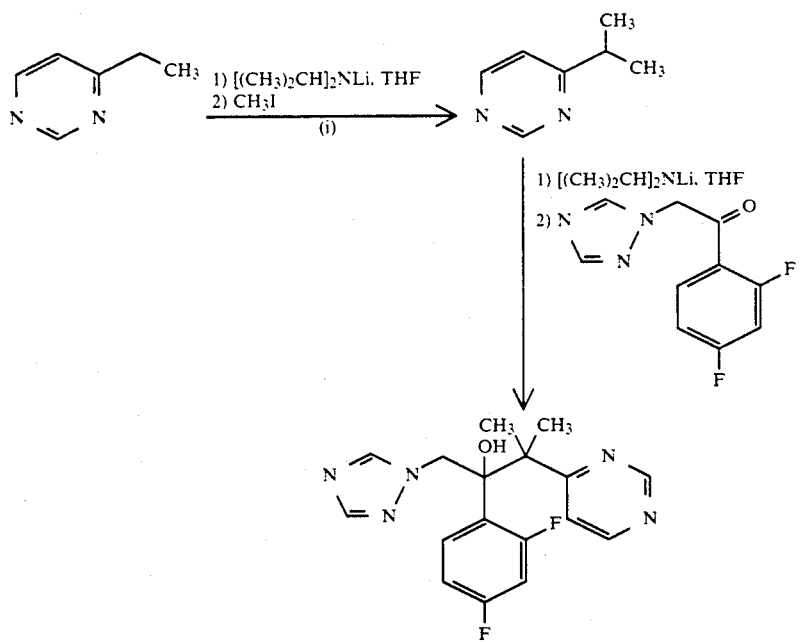

(i) 4-(1-Methylethyl)pyrimidine

A solution of lithium diisopropylamide was prepared as described in Example 1(i) from diisopropylamine (6.88 g) and n-butyllithium (27.0 ml of a 2.5M solution in hexane) in dry tetrahydrofuran (180 ml) under an atmosphere of dry nitrogen. To this solution at −70°, a solution of 4-ethylpyrimidine (7.35 g) in dry tetrahydrofuran (20 ml) was added dropwise over 0.17 hour. The solution was stirred at −70° for 0.75 hour and then iodomethane (11.60 g) was added. The mixture was stirred for a further 3 hours and then warmed to room temperature. Water was added and the solution was evaporated to low bulk, then partitioned between ethyl acetate and water. The organic layer was separated, the aqueous layer was extracted three times with ethyl acetate and the organic fractions were combined and dried ($Na_2SO_4$). Evaporation of the solvent gave an oil which was chromatographed on silica gel, using dichloromethane/ether (9:1) as eluant. The fractions containing the product were combined and evaporated, and the residual oil was distilled to give the title compound, (3.14 g), b.p. 52°–56° at 15 mm.

(ii) 2-(2,4-Difluorophenyl)-3-methyl-3-(pyrimidin-4-yl)-1-(1H-1,2,4-triazol-1-yl)butan-2-ol Treatment of the product of part (i) (2.46 g) with lithium diisopropylamide (0.02 mole) in dry tetrahydrofuran followed by 1-(2,4-difluorophenyl)-2-(1H-1,2,4-triazol-1-yl)ethanone (4.49 g) according to the method of Example 3 gave the title compound, (0.185 g), m.p. 126°–127° (from ether).

Analysis %: Found: C,59.15; H,4.87; N,20.41; C$_{17}$H$_{17}$F$_2$N$_5$O requires: C,59.12; H,4.96; N,20.28.

EXAMPLE 9

2-(2,4-Difluorophenyl)-3-(pyridazin-4-yl)-1-(1H-1,2,4-triazol-1-yl)butan-2-ol

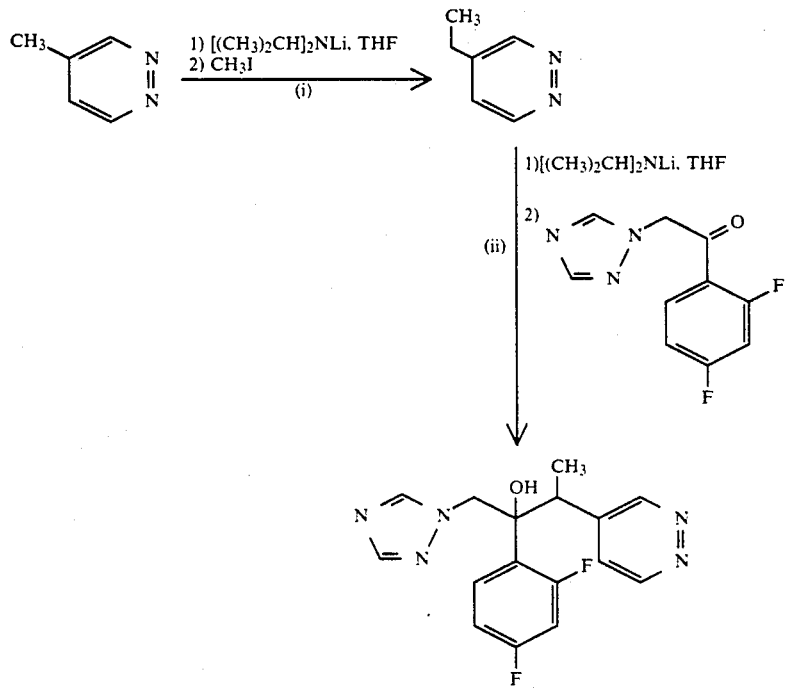

(i) 4-Ethylpyridazine

A solution of lithium diisopropylamide was prepared as described in Example 1(i) from diisopropylamine (17.9 g) and n-butyllithium (70.4 ml of a 2.5M solution in hexane) in dry tetrahydrofuran (300 ml) under an atmosphere of dry nitrogen. To this solution at −70° was added 4-methylpyridazine, dropwise with stirring, ensuring that the temperature did not rise above −60°. Iodomethane (27.25 g) was added slowly with stirring, the solution was stirred at −70° for 1 hour and then allowed to warm to room temperature. Water was added and the solution was evaporated to low bulk. The solution was extracted three times with dichloromethane and the combined extracts were dried (Na$_2$SO$_4$) and evaporated. The residue was chromatographed on silica gel using ethyl acetate as eluant. The product fractions were combined and evaporated, and the residual oil was distilled to give the title compound, (10.4 g), b.p. 65°–66° at 0.1 mm.

N.M.R. (300 MHz): δ (CDCl$_3$)=1.21 (t, 3H, J=7.6 Hz, CH$_2$CH$_3$), 2.61 (q, 2H, J=7.6 Hz, CH$_2$CH$_3$), 7.24 (m, 1H, H$_{arom}$), 8.97 (m, 2H, H$_{arom}$) p.p.m.

(ii)
2-(2,4-Difluorophenyl)-3-(pyridazin-4-yl)-1-(1H-1,2,4-triazol-1-yl)butan-2-ol A solution of lithium diisopropylamide was prepared as described in Example 1(i) from diisopropylamine (2.02 g) and n-butyllithium (8.0 ml of a 2.5M solution in hexane) in dry tetrahydrofuran (60 ml). To this solution at −70° was added 4-ethylpyridazine (2.16 g), dropwise with stirring. The yellow solution was stirred for 0.4 hour at −70° and then a solution of 1-(2,4-difluorophenyl)-2-(1H-1,2,4-triazol-1-yl)ethanone (4.46 g) in dry tetrahydrofuran (20 ml) was added, keeping the temperature below −65°. The solution was stirred for a further 1 hour at this temperature and then acetic acid (1 ml) was added. The solution was allowed to warm to room temperature and diluted with water. The mixture was extracted three times with ethyl acetate and the combined organic extracts were washed with water and dried (Na$_2$SO$_4$). Evaporation of the solvent gave the crude product. Further crude product was obtained by extraction of the combined aqueous layers with dichloromethane. Both crops of crude product thus obtained were combined and chromatographed on silica gel. Elution with dichloromethane/methanol (50:1) first gave ketone starting material. Further elution with the same solvent gave, after combination and evaporation of appropriate fractions, the title compound, diastereoisomeric pair A, (0.98 g), m.p. 172°–174° (from dichloromethane/ether).

Analysis %: Found: C,57.80; H,4.57; N,21.08; C$_{16}$H$_{15}$F$_2$N$_5$O requires: C,58.00; H,4.56; N,21.14.

Further elution with dichloromethane/methanol (50:1) gave, after combination and evaporation of appropriate fractions, the title compound, diastereoisomeric pair B, (1.58 g), m.p. 187°–188° (from acetonitrile).

Analysis %: Found: C,58.00; H,4.54; N,21.05; C$_{16}$H$_{15}$F$_2$N$_5$O requires: C,58.00; H,4.56; N,21.14.

EXAMPLE 10

2-(2,4-Dichlorophenyl)-3-(pyridazin-4-yl)-1-(1H-1,2,4-triazol-1-yl)butan-2-ol

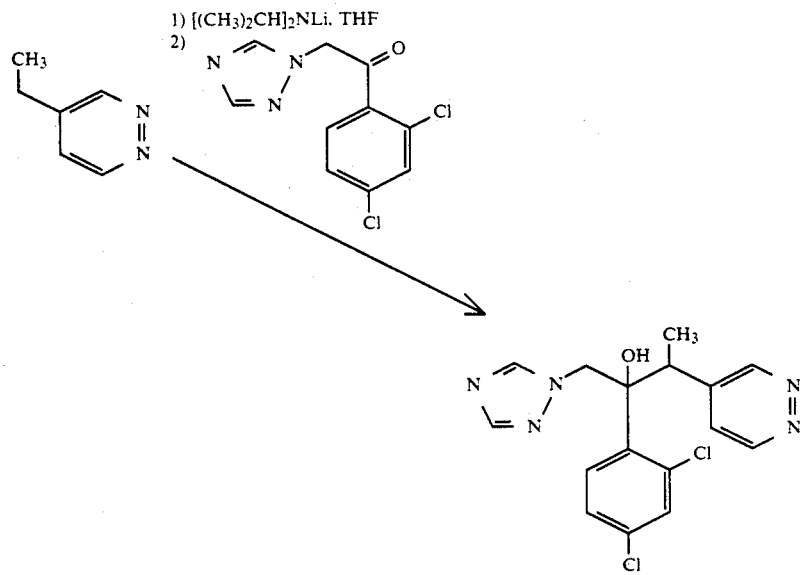

Treatment of 4-ethylpyridazine (2.16 g) with lithium diisopropylamide (0.02 mole) in dry tetrahydrofuran followed by 1-(2,4-dichlorophenyl)-2-(1H-1,2,4-triazol-1-yl)ethanone (5.12 g) according to the method of Example 9(ii) gave the title compound, diastereoisomeric pair A, (1.24 g), m.p. 174°–177°;

Analysis %: Found: C,52.41; H,4.08; N,18.85; $C_{16}H_{15}Cl_2N_5O$ requires: C,52.75; H,4.15; N,19.23.

Analysis %: Found: C,52.22; H,4.12; N,19.05; $C_{16}H_{15}Cl_2N_5O$ requires: C,52.75; H,4.15; N,19.23.

and the title compound, diastereoisomeric pair B, (1.45 g), m.p. 173°–176°.

EXAMPLE 11

2-(2,4-Difluorophenyl)-3-(pyrazin-2-yl)-1-(1H-1,2,4-triazol-1-yl)butan-2-ol

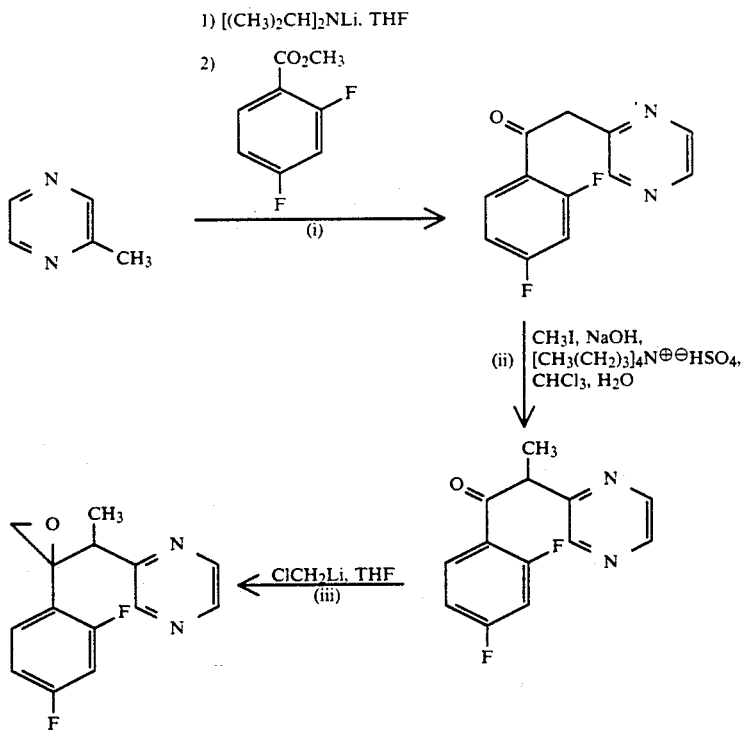

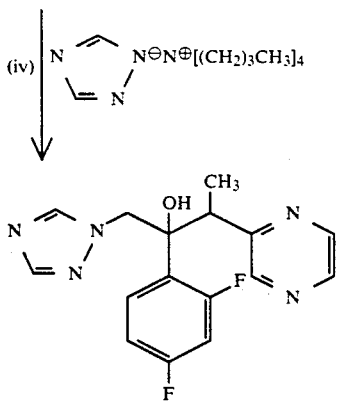

(i) 1-(2,4-Difluorophenyl)-2-(pyrazin-2-yl)ethanone

A solution of lithium diisopropylamide was prepared using n-butyllithium (20 ml of a 2.5M solution in hexane) and diisopropylamine (5.06 g) in dry tetrahydrofuran (100 ml) under an atmosphere of dry nitrogen as described in Example 1(i). To this solution at −70° was added 2-methylpyrazine (4.70 g) and the purple solution resulting was stirred at −70° for 0.5 hour. A solution of methyl 2,4-difluorobenzoate (8.60 g) in dry tetrahydrofuran (75 ml) was added over 0.5 hour and stirring was continued at −70° for a further 0.5 hour. Acetic acid (10 ml) was added and the temperature was allowed to rise to room temperature. The solution was diluted with water and the pH was adjusted to 7 with sodium bicarbonate. The mixture was extracted three times with ethyl acetate and the combined organic extracts were washed with water and dried ($Na_2SO_4$). The solvent was evaporated and the residue was chromatographed on silica gel. Elution with ethyl acetate/hexane (3:7) gave, after combination and evaporation of appropriate fractions, a solid which was crystallised from hexane to give the title compound, (5.90 g), m.p. 107°–108°.

Analysis %: Found: C,61.50; H,3.32; N,12.02; $C_{12}H_8F_2N_2O$ requires: C,61.54; H,3.44; N,11.96.

(ii) 1-(2,4-Difluorophenyl)-2-(pyrazin-2-yl)propan-1-one

A solution of sodium hydroxide (1.98 g) in water (40 ml) was added dropwise to a stirred, ice-cooled solution of the product of part (i) (5.80 g), iodomethane (8.79 g) and tetra-n-butylammonium hydrogen sulphate (8.40 g) in chloroform (40 ml). The mixture was stirred vigorously at room temperature for 3 hours and then diluted with water and dichloromethane. Acetic acid (3 ml) was added and the pH of the aqueous layer was adjusted to 7 with sodium bicarbonate. The organic layer was separated, washed twice with water and dried ($Na_2SO_4$). Evaporation of the solvent gave the crude product as an oil (5.57 g) which was used without further purification (the presence of 10% of the starting material [the product of part (i)] was indicated by N.M.R. spectroscopy).

(iii) 2-(2,4-Difluorophenyl)-2-(1-[pyrazin-2-yl]ethyl)oxirane n-Butyllithium (9.3 ml of a 2.5M solution in hexane) was added to a stirred, cooled (−70°) solution of the product of part (ii) (5.50 g) and bromochloromethane (3.16 g) in dry tetrahydrofuran (125 ml) under an atmosphere of dry nitrogen, at such a rate that the temperature did not rise above −65°. The solution was stirred at −70° for 6 hours and then at room temperature for 18 hours. The solution was diluted with water and extracted three times with ethyl acetate. The combined organic extracts were washed with water and dried ($Na_2SO_4$). Evaporation of the solvent gave an oil which was chromatographed on silica gel. Elution with ethyl acetate/hexane (1:5) gave an oil (4.80 g) which was shown by N.M.R. spectroscopy to contain ca. 70% of the title compound together with impurities. The product was used directly without further purification.

(iv) 2-(2,4-Difluorophenyl)-3-(pyrazin-2-yl)-1-(1H-1,2,4-triazol-1-yl)butan-2-ol 1H-1,2,4-Triazole tetra-n-butylammonium salt (see U.S. Pat. No. 4,259,505) (5.45 g) was added to a stirred solution of the product of part (iii) (2.30 g) in dry tetrahydrofuran (25 ml) at room temperature and stirring was continued for 4 days. The solvent was then evaporated and the residue was partitioned between water and ethyl acetate. Acetic acid (1 ml) was added and the mixture was filtered through Avicel (Trade Mark for a cellulose-based filtration aid). The organic layer was separated, washed three times with water and dried ($Na_2SO_4$). The solvent was evaporated and the residue was chromatographed on silica gel. The column was first eluted with ethyl acetate/hexane (3:2) to remove impurities. Further elution with ethyl acetate/hexane (9:1) gave, after combination and evaporation of appropriate fractions, the title compound, diastereoisomeric pair A, (0.85 g), m.p. 107°–109° (from dichloromethane/hexane).

Analysis %: Found: C,57.76; H,4.44; N,21.31; $C_{16}H_{15}F_2N_5O$ requires: C,58.00; H,4.56; N,21.14.

Further elution with ethyl acetate/methanol (19:1) gave, after combination and evaporation of appropriate fractions, the title compound, diastereoisomeric pair B, (0.29 g), m.p. 133°–135° (from dichloromethane/hexane).

Analysis %: Found: C,57.82; H,4.53; N,21.00; $C_{16}H_{15}F_2N_5O$ requires: C,58.00; H,4.56; N,21.14.

EXAMPLE 12

2-(2,4-Difluorophenyl)-3-(pyridazin-3-yl)-1-(1H-1,2,4-triazol-1-yl)butan-2-ol

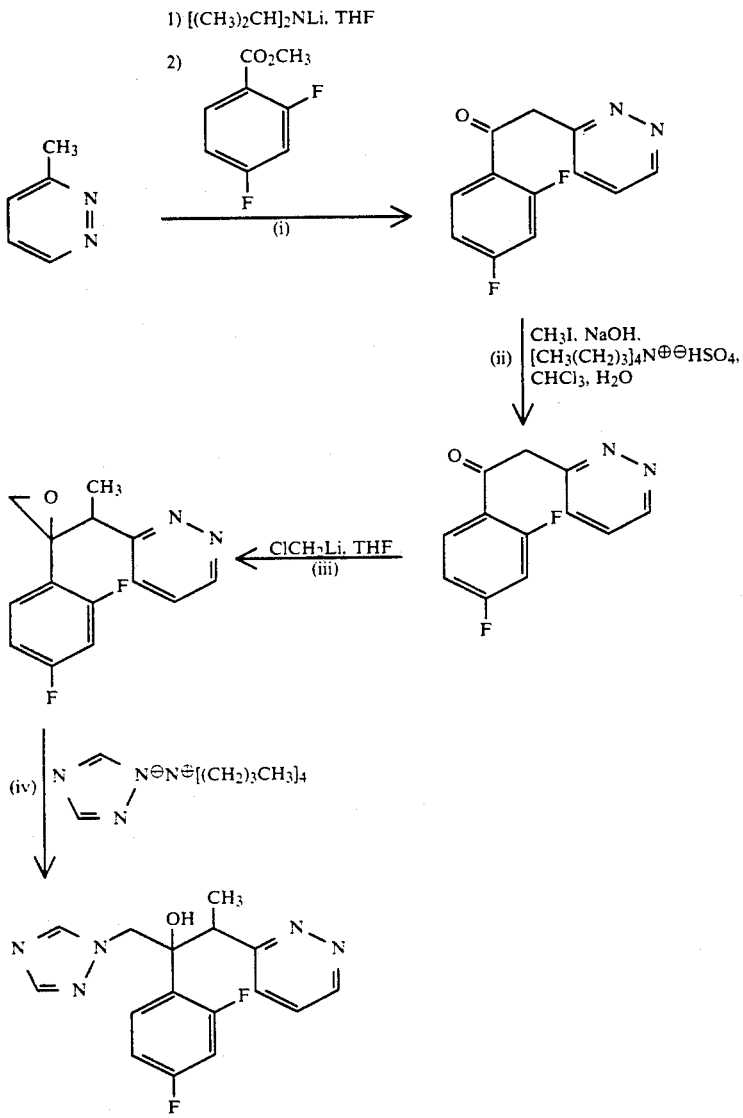

(iii)
2-(2,4-Difluorophenyl)-2-(1-[pyridazin-3-yl]ethyl)oxirane

(i) 1-(2,4-Difluorophenyl)-2-(pyridazin-3-yl)ethanone

Treatment of 3-methylpyridazine (4.70 g) with lithium diisopropylamide (0.05 mole) in dry tetrahydrofuran followed by methyl 2,4-difluorobenzoate (8.60 g) according to the method of Example 11(i) gave the title compound, (3.40 g), m.p. 115.5°–117.5° (from ether).

Analysis %: Found: C,61.68; H,3.40; N,11.77; $C_{12}H_8F_2N_2O$ requires: C,61.54; H,3.44; N,11.96.

(ii) 1-(2,4-Difluorophenyl)-2-(pyridazin-3-yl)propan-1-one

Methylation of the product of part (i) (3.30 g) with iodomethane (5.0 g) according to the method of Example 11(ii) gave the title compound as a gum (2.25 g) which was used directly in the next stage.

Treatment of the product of part (ii) (2.0 g) with bromochloromethane (1.15 g) and n-butyllithium (5.28 ml of a 1.6M solution in hexane) according to the method of Example 11(iii) gave the title compound as a gum (1.20 g) which was used directly in the next stage.

(iv) 2-(2,4-Difluorophenyl)-3-(pyridazin-3-yl)-1-(1H-1,2,4-triazol-1-yl)butan-2-ol Treatment of the product of part (iii) (1.15 g) with 1H-1,2,4-triazole sodium salt (0.80 g) in N,N-dimethylformamide (15 ml) according to the method of Example 1(ii), followed by chromatography of the crude product on silica gel using dichloromethane/methanol (50:1) as eluant, first gave, after combination and evaporation of appropriate fractions, the title compound, diastereoisomeric pair A, (0.35 g), m.p. 134°–135° (from ether).

Analysis %: Found: C,58.04; H,4.57; N,20.87; $C_{16}H_{15}F_2N_5O$ requires: C,58.00; H,4.56; N,21.14.

Further elution with the same solvent gave, after combination and evaporation of appropriate fractions, the title compound, diastereoisomeric pair B, as an amorphous foam (84 mg).

N.M.R. (300 MHz): δ (CDCl$_3$)=1.20 (d, 2H, J=7.2 Hz, CH$_3$), 3.95 (q, 1H, J=7.2 Hz, CHCH$_3$), 4.04 and 4.91 (d, 1H, J=14.2 Hz, CH$_2$), 6.18 (s, 1H, OH), 6.82 (m, 2H, H$_{arom}$), 7.67 (m, 1H, H$_{arom}$), 7.56 (m, 2H, H$_{arom}$), 7.64 (s, 1H, H$_{arom}$), 7.94 (s, 1H, H$_{arom}$), 9.18 (m, 1H, H$_{arom}$) p.p.m.

EXAMPLE 13

2-(2,4-Difluorophenyl)-3-(pyrimidin-2-yl)-1-(1H-1,2,4-triazol-1-yl)butan-2-ol

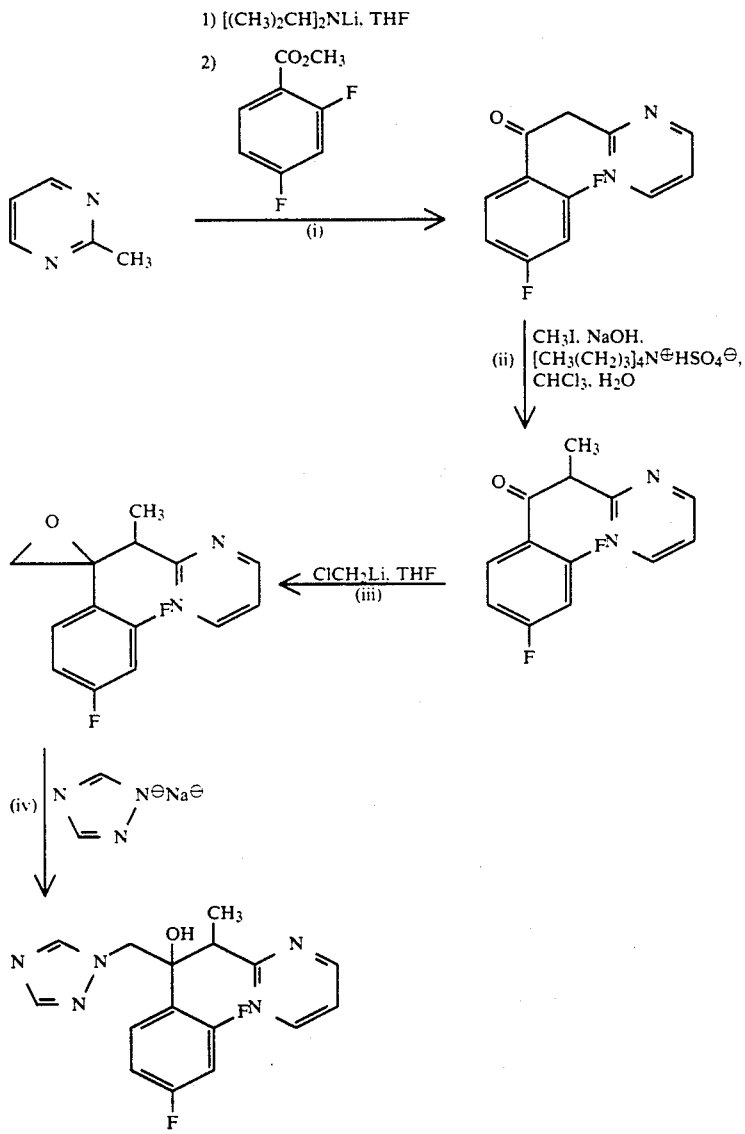

(i) 1-(2,4-Difluorophenyl)-2-(pyrimidin-2-yl)ethanone

Treatment of 2-methylpyrimidine (8.50 g) with lithium diisopropylamide (0.09 mole) in dry tetrahydrofuran followed by methyl 2,4-difluorobenzoate (15.5 g) according to the method of Example 11(i) gave the title compound (3.65 g), m.p. 86°-88° (from hexane).

Analysis %: Found: C,61.67; H,3.41; N,12.01; C$_{12}$H$_8$F$_2$N$_2$O requires: C,61.54; H,3.44; N,11.96.

(ii) 1-(2,4-Difluorophenyl)-2-(pyrimidin-2-yl)propan-1-one

Methylation of the product of part (i) (3.50 g) with iodomethane (5.32 g) according to the method of Example 11(ii) gave the title compound (3.30 g), m.p. 118°-119°.

Analysis %: Found: C,63.17; H,4.18; N,11.02; C$_{13}$H$_{10}$F$_2$N$_2$O requires: C,62.90; H,4.06; N,11.29.

(iii) 2-(2,4-Difluorophenyl)-2-[1-(pyrimidin-2-yl)ethyl]oxirane

Treatment of the product of part (ii) (3.10 g) with chloromethyllithium (prepared from bromochloromethane (1.78 g) and a 1.6M solution of n-butyllithium in hexane (8.20 ml)) according to the method of Example 11(iii) gave the title compound as a gum (2.25 g), which was used directly in the next stage.

(iv) 2-(2,4-Difluorophenyl)-3-(pyrimidin-2-yl)-1-(1H-1,2,4-triazol-1-yl)butan-2-ol

EXAMPLE 14

2-(2,4-Difluorophenyl)-3-(pyridin-3-yl)-1-(1H-1,2,4-triazol-1-yl)butan-2-ol

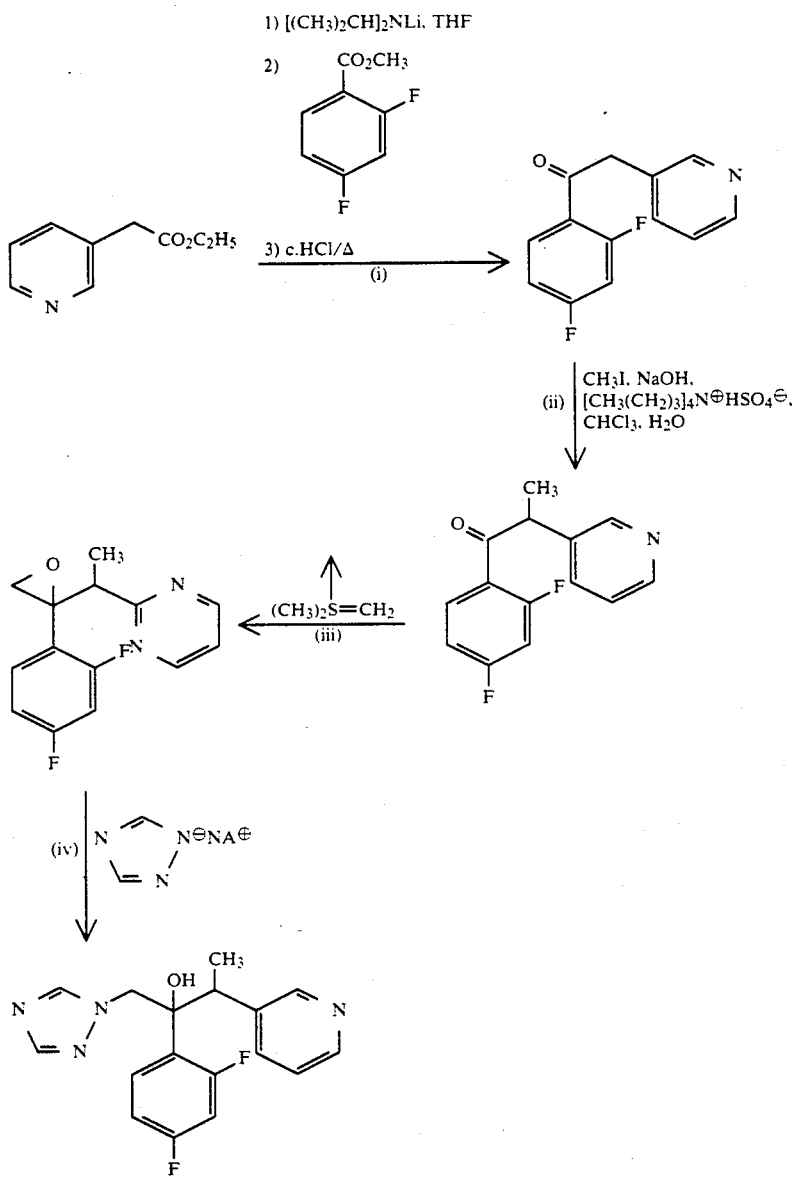

Treatment of the product of part (iii) (0.80 g) with 1H-1,2,4-triazole, sodium salt (0.82 g) in N,N-dimethylformamide according to the method of Example 12(iv), followed by chromatography of the crude product on silica gel using ethyl acetate as eluant, first gave, after combination and evaporation of appropriate fractions, the title compound, diastereoisomeric pair A, (0.26 g), m.p. 193°-195° (from dichloromethane/ether).

Analysis %: Found: C,57.50; H,4.57; N,21.03; $C_{16}H_{15}F_2N_5O$ requires: C,58.00; H,4.56; N,21.14.

Further elution with ethyl acetate/methanol (20:1) gave, after combination and evaporation of appropriate fractions, the title compound, diastereoisomeric pair B, (0.055 g), m.p. 104°-106° (from ether).

Analysis %: Found: C,57.27; H,4.37; N,20.55; $C_{16}H_{15}F_2N_5O$ requires: C,58.00; H,4.56; N,21.14.

(i) 1-(2,4-Difluorophenyl)-2-(pyridin-3-yl)ethanone

A solution of lithium diisopropylamide was prepared using n-butyllithium (66 ml of a 1.6M solution in hexane) and diisopropylamine (10.8 g) in dry tetrahydrofuran (200 ml) under an atmosphere of dry nitrogen as described in Example 1(i). Ethyl 3-pyridylacetate was added dropwise to this solution at −70°. The thick mixture was stirred at −70° for 0.25 hour and then a solution of methyl 2,4-difluorobenzoate (18.36 g) in dry tetrahydrofuran (100 ml) was added over 0.05 hour. The cooling bath was removed and the mixture was stirred at room temperature for 5 hours. Acetic acid (12 ml) was added and the mixture was diluted with water and ethyl acetate. The organic layer was separated, dried ($Na_2SO_4$) and evaporated to give an oil which was heated under reflux in concentrated hydrochloric acid (40 ml) for 5 hours. The solution was evaporated, the residue was dissolved in water and concentrated ammonia solution was added to ca. pH7. The mixture was extracted twice with ethyl acetate and the combined extracts were washed with brine and dried (Na$_2$SO$_4$). Evaporation of the solvent gave an oil which was chromatographed on silica gel. Elution with dichloromethane/ethyl acetate (70:30) gave the title compound as an oil (6.98 g) which was used directly in the next stage.

(ii) 1-(2,4-Difluorophenyl)-2-(pyridin-3-yl)propan-1-one

Methylation of the product of part (i) (5.0 g) with iodomethane (7.60 g) according to the method of Example 11(ii) gave the title compound as an oil (3.90 g) which was used directly in the next stage.

(iii)
2-(2,4-Difluorophenyl)-2-[1-(pyridin-3-yl)ethyl]oxirane

A solution of dimethylsulphoxonium methylide (36.5 ml of a 0.6M solution in tetrahydrofuran) was added dropwise to a stirred solution of the product of part (ii) (4.36 g) in tetrahydrofuran (35 ml) at −20°. The solution was allowed to warm to room temperature and stirring was continued for 18 hours and then diluted with water. The mixture was extracted with ethyl acetate and the combined extracts were dried (Na$_2$SO$_4$). Evaporation of the solvent gave the title compound as an oil (4.50 g) which was used directly in the next stage.

(iv)
2-(2,4-Difluorophenyl)-3-(pyridin-3-yl)-1-(1H-1,2,4-triazol-1-yl)butan-2-ol Treatment of the product of part (iii) (4.30 g) with 1H-1,2,4-triazole, sodium salt (3.0 g) in N,N-dimethylformamide (50 ml) according to the method of Example 1(ii), followed by chromatography of the crude product on silica gel using ethyl acetate as eluant, first gave, after combination and evaporation of appropriate fractions, the title compound, diastereoisomeric pair A, (1.13 g), m.p. 113°-114° (from ether).

Analysis %: Found: C,62.10; H,4.90; N,16.96; C$_{17}$H$_{16}$F$_2$N$_4$O requires: C,61.81; H,4.88; N,16.96.

Further elution with ethyl acetate/methanol (20:1) gave, after combination and evaporation of appropriate fractions, the title compound, diastereoisomeric pair B, (1.25 g), m.p. 115°-116° (from ether).

Analysis %: Found: C,61.92; H,4.95; N,16.87; C$_{17}$H$_{16}$F$_2$N$_4$O requires: C,61.81; H,4.88; N,16.96.

EXAMPLE 15

2-(2,4-Difluorophenyl)-3-(2-cyanopyridin-4-yl)-1-(1H-1,2,4-triazol-1-yl)butan-2-ol

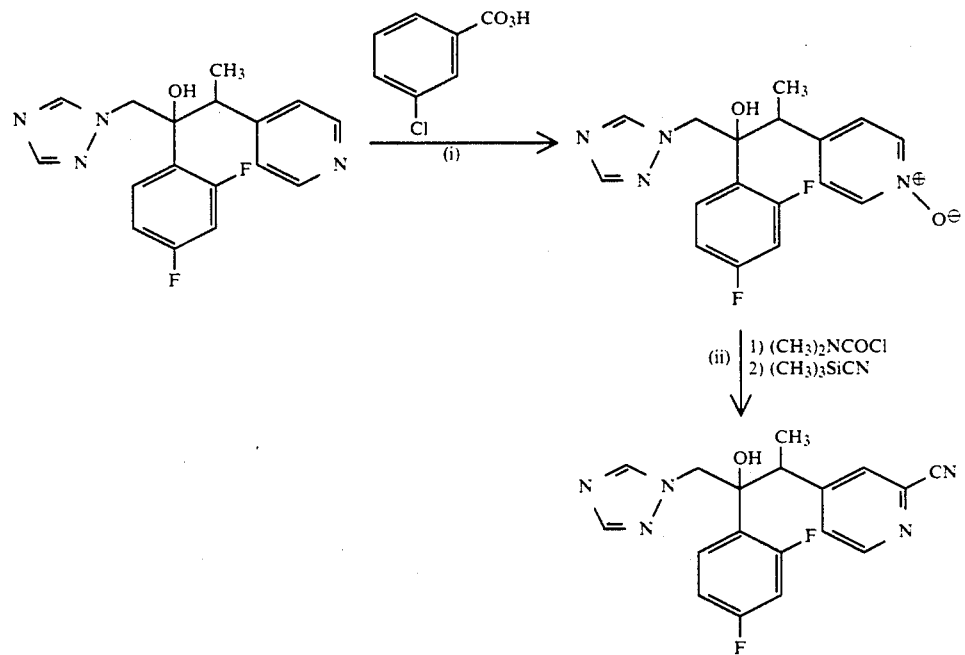

(i)
2-(2,4-Difluorophenyl)-3-(1-oxidopyridin-4-yl)-1-(1H-1,2,4-triazol-1-yl)butan-2-ol A solution of 2-(2,4-difluorophenyl)-3-(pyridin-4-yl)-1-(1H-1,2,4-triazol-1-yl)butan-2-ol (diastereoisomeric pair B from Example 2) (20.0 g) and 85% w/w 3-chloroperoxybenzoic acid (12.3 g) in dichloromethane (250 ml) was stirred at room temperature for 18 hours. Further 3-chloroperoxybenzoic acid (2.50 g) was then added and stirring was continued for 24 hours. The solution was evaporated and the residue was dissolved in ether. A solid formed on standing which was filtered off and chromatographed on silica gel. Elution with dichloromethane/methanol/0.88 ammonia solution (100:4:0.5) gave the title compound as a solid, (20.0 g), m.p. 195°-198°.

(ii)
2-(2,4-Difluorophenyl)-3-(2-cyanopyridin-4-yl)-1-(1H-1,2,4-triazol-1-yl)butan-2-ol A mixture of the product of part (i) (20.0 g) and N,N-dimethylcarbamoyl chloride (6.80 g) in dichloromethane (250 ml) was stirred at room temperature for 2.5 days, giving a clear solution. Trimethylsilyl cyanide (6.35 g) was added and stirring was continued for a further 48 hours. Additional quantities of N,N-dimethylcarbamoyl chloride (1.30 g) and trimethylsilyl cyanide (1.30 g) were then added and the solution was stirred for a further 36 hours. The reaction was then washed successively with 10% potassium carbonate solution, brine and then dried (MgSO$_4$). Evaporation of the solvent gave a solid which was stirred with ether and filtered to give the title compound, (19.2 g), m.p. 188°-189°.

Analysis %: Found: C,60.89; H,4.24; N,19.44; C$_{18}$H$_{15}$F$_2$N$_5$O requires: C,60.84; H,4.25; N,19.71.

EXAMPLE 16

2-(2,4-Difluorophenyl)-3-(6-cyanopyridin-2-yl)-1-(1H-1,2,4-triazol-1-yl)butan-2-ol (i)
2-(2,4-Difluorophenyl)-3-(1-oxidopyridin-2-yl)-1-(1H-1,2,4-triazol-1-yl)butan-2-ol A solution of 2-(2,4-difluorophenyl)-3-(pyridin-2-yl)-1-(1H-1,2,4-triazol-1-yl)butan-2-ol (diasatereoisomeric pair B from Example 1) (1.60 g) and 85% w/w 3-chloroperoxybenzoic acid (1.60 g) in dichloromethane (10 ml) was stirred at room temperature for 36 hours and then worked up as described in Example 15(i) to give the title compound, (0.92 g), m.p. 159°-160°.

Analysis %: Found: C,59.27; H,4.96; N,16.58; C$_{17}$H$_{16}$F$_2$N$_4$O$_2$ requires: C,58.96; H,4.45; N,15.47.

(ii)
2-(2,4-Difluorophenyl)-3-(6-cyanopyridin-2-yl)-1-(1H-1,2,4-triazol-1-yl)butan-2-ol A mixture of the product of part (i) (0.90 g), N,N-dimethylcarbamoyl chloride (0.80 g) and trimethylsilyl cyanide (0.80 g) in dichloromethane (10 ml) was stirred at room temperature for 7 days and the resulting solution was evaporated. The residue was treated with 5N hydrochloric acid (10 ml) and the mixture was agitated in an ultrasonic bath for 0.05 hour to give a clear solution. A solid formed on standing which was filtered off, washed with acetone followed by ether, and dried to give the title compound as the hydrochloride salt, (0.28 g), m.p. 219° (with decomposition).

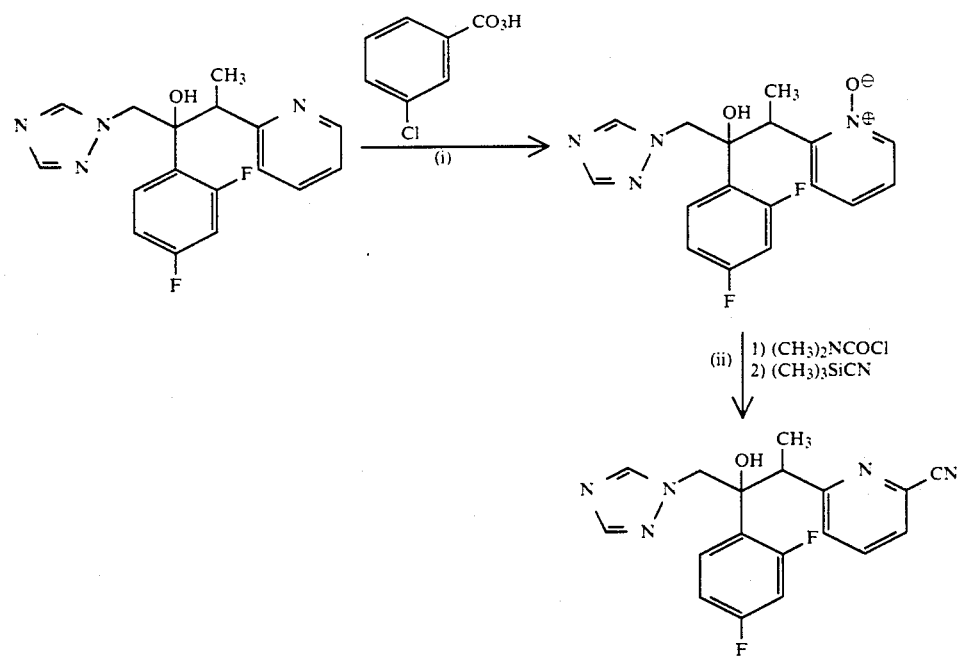

Analysis %: Found: C,55.19; H,4.10; N,18.00; C$_{18}$H$_{15}$F$_2$N$_5$O.HCl requires: C,55.18; H,4.12; N,17.87.

The acidic filtrate was basified (ca. pH8) with 0.88 ammonia solution and the solution was extracted with dichloromethane. The organic extract was dried (MgSO$_4$) and evaporated. The residue was triturated with ether and filtered to give the title compound as the free base, (0.13 g), m.p. 144°-146°.

Analysis %: Found: C,60.84; H,4.25; N,19.71; C$_{18}$H$_{15}$F$_2$N$_5$O requires: C,60.48; H,4.17; N,19.90.

EXAMPLE 17

2-(2,4-Difluorophenyl)-3-(2-cyanopyridin-3-yl)-1-(1H-1,2,4-triazol-1-yl)butan-2-ol and
2-(2,4-difluorophenyl)-3-(2-cyanopyridin-5-yl)-1-(1H-1,2,4-triazol-1-yl)butan-2-ol

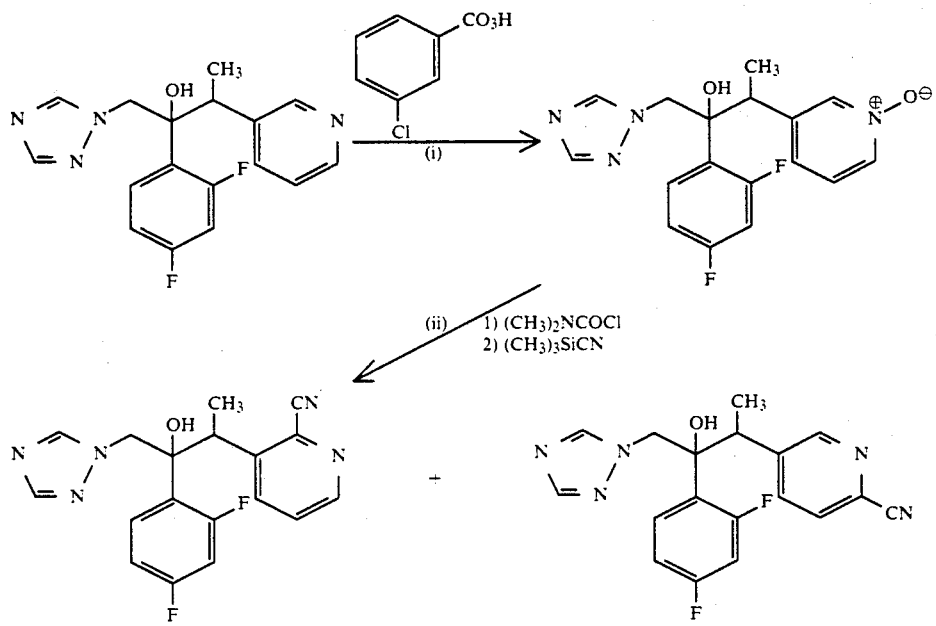

(i)
2-(2,4-Difluorophenyl)-3-(1-oxidopyridin-3-yl)-1-(1H-1,2,4-triazol-1-yl)butan-2-ol A solution of 2-(2,4-difluorophenyl)-3-(pyridin-3-yl)-1-(1H-1,2,4-triazol-1-yl)butan-2-ol (diastereoisomeric pair B from Example 14) (1.00 g) and 85% w/w 3-chloroperoxybenzoic acid (1.30 g) in dichloromethane (20 ml) was stirred at room temperature for 18 hours and then evaporated. The residue was stirred with ether and the solid was filtered off and dried to give the title compound (0.93 g), m.p. 190°–193°.

(ii)
2-(2,4-Difluorophenyl)-3-(2-cyanopyridin-3-yl)-1-(1H-1,2,4-triazol-yl)butan-2-ol and
2-(2,4-difluorophenyl)-3-(2-cyanopyridin-5-yl)-1-(1H-1,2,4-triazol-1-yl)butan-2-ol A mixture of the product of part (i) (0.93 g) and N,N-dimethylcarbamoyl chloride (0.40 g) in dichloromethane (10 ml) was stirred at room temperature overnight. Trimethylsilyl cyanide (0.40 g) was added and stirring was continued for a further 60 hours. The solution was washed with 10% sodium carbonate solution and the aqueous layer was separated and washed with dichloromethane. The organic layers were combined, dried (MgSO$_4$) and evaporated. The residue was chromatographed on silica gel using hexane/isopropanol (4:1) as eluant to give 2-(2,4-difluorophenyl)-3-(2-cyanopyridin-5-yl)-1-(1H-1,2,4-triazol-1-yl)butan-2-ol, (0.18 g), m.p. 136°–141°.

Analysis %: Found: C,60.89; H,4.59; N,19.47; C$_{18}$H$_{15}$F$_2$N$_5$O requires: C,60.84; H,4.25; N,19.71.

N.M.R. (300 MHz): δ(CDCl$_3$)=1.17 (d, 3H, J=7.1 Hz, CH$_3$), 3.47 (q, 1H, J=7.1 Hz, CHCH$_3$), 3.81 and 4.85 (d, 1H, J=13.8 Hz, CH$_2$), 5.19 (s, 1H, OH), 6.81 (m, 2H, H$_{arom}$), 7.47 (m, 1H, H$_{arom}$), 7.75 (d, 1H, J=8 Hz, pyridine H-3), 7.76 and 7.79 (s, 1H, triazole H), 8.10 (m, 1H, pyridine H-4), 8.80 (d, 1H, J=1.8 Hz, pyridine H-6) p.p.m.

Further elution with the same solvent mixture gave, after combination and evaporation of appropriate fractions, 2-(2,4-difluorophenyl)-3-(2-cyanopyridin-3-yl)-1-(1H-1,2,4-triazol-1-yl)butan-2-ol (0.23 g), m.p. 180°–182°.

Analysis %: Found: C,60.85; H,4.33; N,19.51; C$_{18}$H$_{15}$F$_2$N$_5$O requires: C,60.84; H,4.25; N,19.71.

N.M.R. (300 MHz): δ(CDCl$_3$)=1.17 (d, 3H, J=7.0 Hz, CH$_3$), 3.82 and 5.17 (d, 1H, J=13.8 Hz, CH$_2$), 4.05 (q, 1H, J=7.0 Hz, CHCH$_3$), 5.21 (s, 1H, OH), 6.82 (m, 2H, H$_{arom}$), 7.46 (m, 1H, H$_{arom}$), 7.60 (m, 1H, pyridine H-5), 7.76 and 7.83 (s, 1H, triazole H), 8.32 (m, 1H, pyridine H-4), 8.68 (m, 1H, pyridine H-6) p.p.m.

EXAMPLE 18

2-(2,4-Difluorophenyl)-3-(2-cyanopyrimidin-4-yl)-1-(1H-1,2,4-triazol-1-yl)butan-2-ol and 2-(2,4-difluorophenyl)-3-(6-cyano-pyrimidin-4-yl)-1-(1H-1,2,4-triazol-1-yl)butan-2-ol

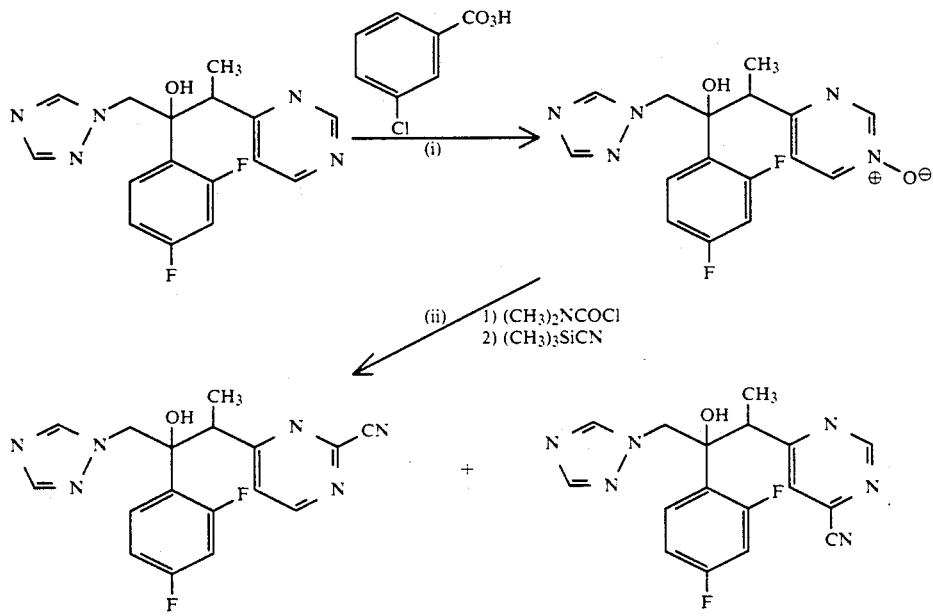

40

(i)
2-(2,4-Difluorophenyl)-3-(1-oxidopyrimidin-4-yl)-1-(1H-1,2,4-triazol-1-yl)butan-2-ol A solution of 2-(2,4-difluorophenyl)-3-(pyrimidin-4-yl)-1-(1H-1,2,4-triazol-1-yl)butan-2-ol (diastereoisomeric pair B from Example 3) (3.31 g) and 85% w/w 3-chloroperoxybenzoic acid (2.03 g) in dichloromethane (20 ml) was stirred at room temperature for 48 hours. An additional 2.03 g of 85% w/w 3-chloroperoxybenzoic acid was added and stirring was continued for a further 18 hours. Work up as described in Example 15(i) gave the title compound, (0.80 g), m.p. 157°–160°.

(ii)
2-(2,4-Difluorophenyl)-3-(2-cyanopyrimidin-4-yl)-1-(1H-1,2,4-triazol-1-yl)butan-2-ol and 2-(2,4-difluorophenyl)-3-(6-cyanopyrimidin-4-yl)-1-(1H-1,2,4-triazol-1-yl)butan-2-ol A mixture of the product of part (i) (0.80 g) and N,N-dimethylcarbamoyl chloride (0.50 g) in dichloromethane (10 ml) was stirred at room temperature for 2 hours. Trimethylsilyl cyanide (0.50 g) was added and stirring was continued for a further 6 days. The solution was evaporated and the residue was chromatographed on silica gel. Elution with dichloromethane/methanol (100:1) gave a product which was rechromatographed on silica gel. Elution was commenced with ether and the polarity of the eluant was gradually increased by the addition of up to 6% (by volume) of methanol. Combination and evaporation of the initial product-containing fractions gave 2-(2,4-difluorophenyl)-3-(6-cyanopyrimidin-4-yl)-1-(1H-1,2,4-triazol-1-yl)butan-2-ol, (30 mg), m.p. 148°–149°.

N.M.R. (300 MHz) δ (CDCl$_3$)=1.16 (d, 3H, J=7.17 Hz, CH$_3$), 3.77 (q, 1H, J=7.17 Hz, CHCH$_3$), 4.09 and 4.88 (d, 1H, J=14.15 Hz, CH$_2$), 5.74 (s, 1H, OH), 6.85 (m, 2H, H$_{arom}$), 7.55 (m, 1H, H$_{arom}$), 7.69 and 7.87 (s, 1H, triazole H), 7.89 (d, 1H, J=1 Hz, pyrimidine H-5), 9.24 (d, 1H, J=1 Hz, pyrimidine H-2) p.p.m.

Further elution gave, after combination and evaporation of appropriate fractions, 2-(2,4-difluorophenyl)-3-(2-cyanopyrimidin-4-yl)-1-(1H-1,2,4-triazol-1-yl)butan-2-ol, (203 mg), m.p. 155°–157°.

Analysis %: Found: C,57.30; H,3.96; N,23.59; C$_{17}$H$_{14}$F$_2$N$_6$O requires: C,57.36; H,3.97; N,23.36.

N.M.R. (300 MHz): δ (CDCl$_3$)=1.17 (d, 3H, J=7.16 Hz, CH$_3$), 3.73 (q, 1H, J=7.16 Hz, CHCH$_3$), 3.99 and 4.99 (d, 1H, J=14.2 Hz, CH$_2$), 5.39 (s, 1H, OH), 6.82 (m, 2H, H$_{arom}$), 7.51 (m, 1H, H$_{arom}$), 7.71 and 7.88 (s, 1H, triazole H), 7.77 (d, 1H, J=5.3 Hz, pyrimidine H-5), 8.84 (d, 1H, J=5.3 Hz, pyrimidine H-6) p.p.m.

EXAMPLE 19

2-(2,4-Difluorophenyl)-3-(2-ethoxycarbonylaminopyridin-4-yl)-1-(1H-1,2,4-triazol-1-yl)butan-2-ol

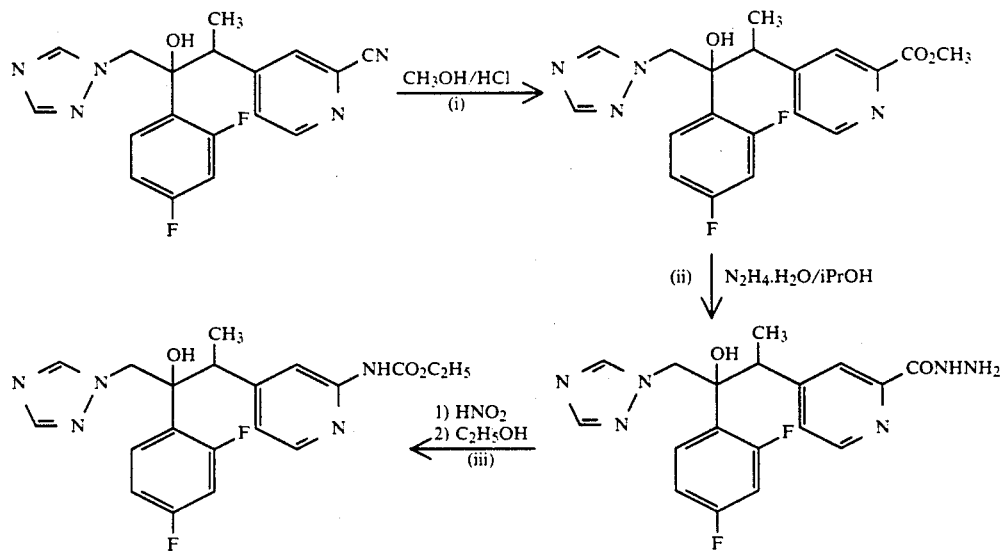

(i)
2-(2,4-Difluorophenyl)-3-(2-methoxycarbonylpyridin-4-yl)-1-(1H-1,2,4-triazol-1-yl)butan-2-ol A suspension of 2-(2,4-difluorophenyl)-3-(2-cyanopyridin-4-yl)-1-(1H-1,2,4-triazol-1-yl)butan-2-ol (see Example 15) (5.0 g) in methanol (50 ml) was saturated with gaseous hydrogen chloride, heated under reflux for 2 hours and then allowed to stand at room temperature for 18 hours. The solution was evaporated and the residue basified with dilute sodium bicarbonate solution. The mixture was extracted several times with dichloromethane and the combined extracts were dried (MgSO₄) and evaporated. Crystallisation of the residue from methyl acetate gave the title compound, (4.90 g), m.p. 182°-183°.

(ii)
4-[3-(2,4-Difluorophenyl)-3-hydroxy-4-(1H-1,2,4-triazol-1-yl)but-2-yl]pyridine-2-carboxylic acid hydrazide A solution of the product of part (i) (3.80 g) and hydrazine hydrate (6.0 ml) in isopropanol (20 ml) was heated under reflux for 2.5 hours and then evaporated. Water was added to the residue and the mixture was extracted several times with dichloromethane. The combined extracts were washed with brine and dried (MgSO₄). Evaporation of the solvent gave the title compound (3.30 g) as an amorphous foam which was used directly in the next stage.

(iii)
2-(2,4-Difluorophenyl)-3-(2-ethoxycarbonylaminopyridin-4-yl)-1-(1H-1,2,4-triazol-1-yl)butan-2-ol The product of part (ii) (1.40 g) was dissolved in 6N hydrochloric acid and the solution was cooled to 0°. A solution of sodium nitrite (0.276 g) in water (2 ml) was added dropwise with stirring, and stirring was continued for 1 hour. The solution was then basified with sodium bicarbonate solution and the resulting mixture was extracted several times with dichloromethane. The combined organic extracts were dried (MgSO₄) and evaporated. The residue was dissolved in ethanol (50 ml) and the solution was heated under reflux for 2.5 hours and then evaporated. The residue was crystallised from ether to give the title compound, (1.12 g), m.p. 177°-179°.

Analysis %: Found: C,57.90; H,5.25; N,16.81; $C_{20}H_{21}F_2N_5O_3$ requires: C,57.55; H,5.07; N,16.78.

EXAMPLE 20

3-(2-Aminopyridin-4-yl)-2-(2,4-difluorophenyl)-1-(1H-1,2,4-triazol-1-yl)butan-2-ol

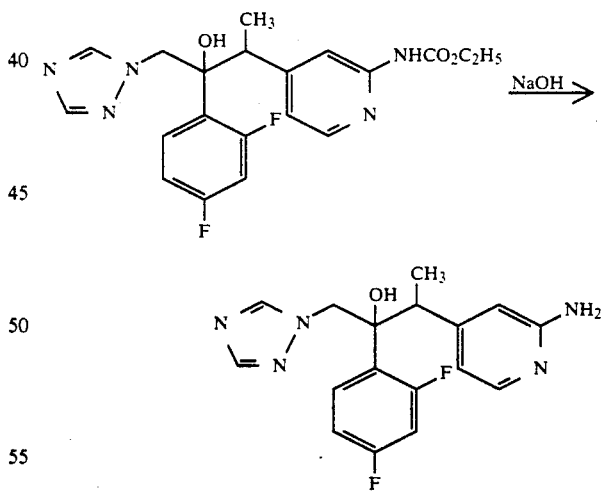

A solution of the product of Example 19 (0.80 g) in ethanol (30 ml) containing 40% sodium hydroxide solution (2.0 ml) was heated under reflux for 2 hours and then evaporated. Water was added to the residue and the mixture was extracted several times with ethyl acetate. The combined organic extracts were dried (MgSO₄) and evaporated to give a gum. The gum was dissolved in ether and the title compound, (0.45 g), crystallised on standing, m.p. 182°-185°.

Analysis %: Found: C,59.34; H,5.03; N,19.92; $C_{17}H_{17}F_2N_5O$ requires: C,59.13; H,4.96; N,20.28.

EXAMPLE 21

2(2,4-Difluorophenyl)-3-(2-ethoxycarbonylaminopyridin-5-yl)-1-(1H-1,2,4-triazol-1-yl)butan-2-ol

EXAMPLE 22

3-(2-Aminopyridin-5-yl)-2-(2,4-difluorophenyl)-1-(1H-1,2,4-triazol-1-yl)butan-2-ol

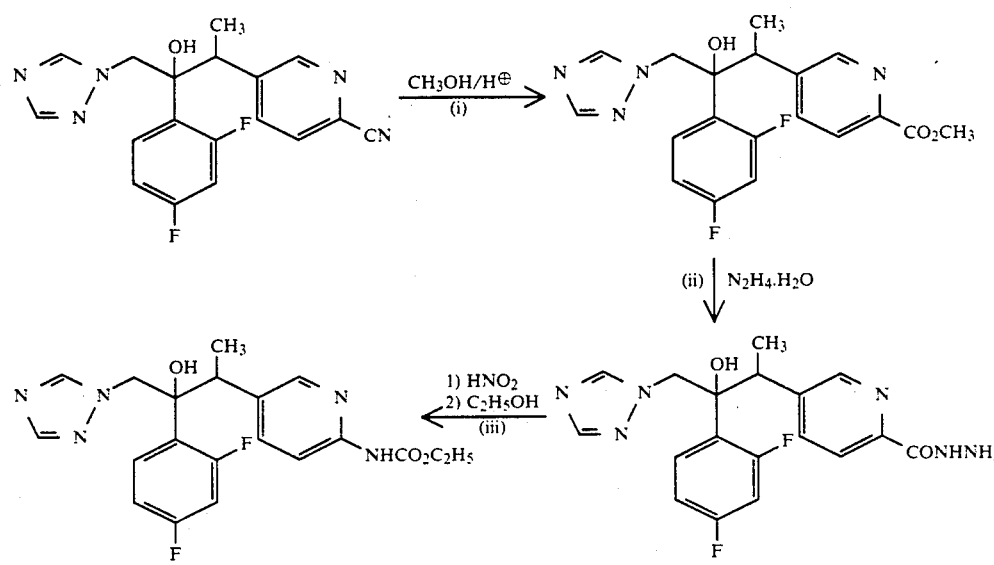

(i)
2-(2,4-Difluorophenyl)-3-(2-methoxycarbonylpyridin-5-yl)-1-(1H-1,2,4-triazol-1-yl)butan-2-ol Treatment of 2-(2,4-difluorophenyl)-3-(2-cyanopyridin-5-yl)-1-(1H-1,2,4-triazol-1-yl)butan-2-ol (see Example 17) (1.0 g) with methanol (20 ml) in the presence of hydrogen chloride according to the method of Example 19 (i) gave the title compound as a gum, (0.75 g), which was used directly in the next step.

(ii)
5-([3-(2,4-Difluorophenyl)-3-hydroxy-4-(1H-1,2,4-triazol-1-yl)]but-2-yl)pyridine-2-carboxylic acid hydrazide Treatment of the product of part (i), (0.75 g), with hydrazine hydrate (2.0 ml) in isopropanol (10 ml) according to the method of Example 19 (ii) gave the title compound, (0.36 g), as an amorphous foam which was used directly in the next stage.

(iii)
2-(2,4-Difluorophenyl)-3-(2-ethoxycarbonylaminopyridin-5-yl)-1-(1H-1,2,4-triazol-1-yl)butan-2-ol Treatment of the product of part (ii) (0.36 g) with nitrous acid followed by heating the resulting azide intermediate in ethanol according to the method of Example 19 (iii) gave a crude product which was chromatographed on silica gel. Elution with ethyl acetate gave, after combination and evaporation of appropriate fractions, a solid which was crystallised from ethyl acetate/ether to give the title compound, (0.12 g), m.p. 167°–168°.

Analysis % : Found: C,57.81; H,5.00; N,16.46; $C_{20}H_{21}F_2N_5O_3$ requires: C,57.55; H,5.07; N,16.78.

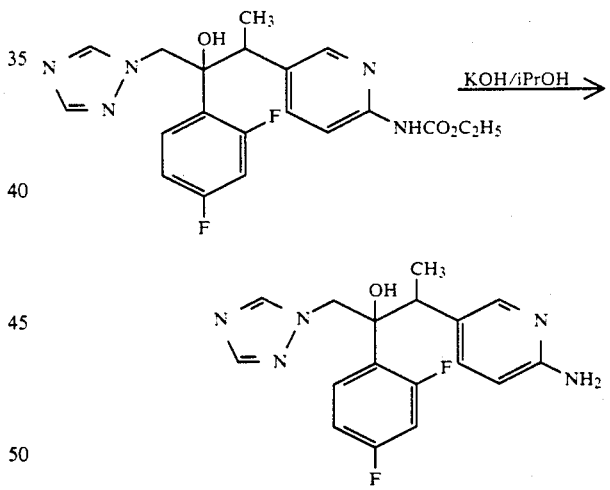

A solution of the product of Example 21 (70 mg) in isopropanol (4 ml) containing 50% aqueous potassium hydroxide (4 drops) was heated under reflux for 4 hours and then evaporated. Water was added to the residue and the mixture was extracted several times with ethyl acetate. The combined organic extracts were washed with water and dried ($MgSO_4$). Evaporation of the solvent gave the title compound as an amorphous foam, (49 mg).

N.M.R. (300 MHz): δ ($CDCl_3$) = 1.06 (d, 3H, J = 7.12 Hz, $CH_3$), 3.23 (q, 1H, J = 7.12 Hz, C$H$CH$_3$), 3.93 and 4.77 (d, 1H, J = 14.2 Hz, $CH_2$), 4.63 (broad s, 2H, $NH_2$), 6.54 (d, 1H, J = 8.5 Hz, pyridine H-3), 6.75 (m, 2H, $H_{arom}$), 7.45 (m, 1H, $H_{arom}$), ca. 7.70 (m, 1H, pyridine H-4), 7.71 and 7.76 (s, 1H, triazole H), 8.04 (s, 1H, pyridine H-6) p.p.m.

EXAMPLE 23
(−)-(2R,3S)-2-(2,4-Difluorophenyl)-3-(pyrimidin-4-yl)-1-(1H-1,2,4-triazol-1-yl)butan-2-ol
(i) 2-Acetoxy-2',4'-difluoroacetophenone
A solution of 2-chloro-2',4'-difluoroacetophenone (19.0 g) and anhydrous sodium acetate (16.4 g) in acetic
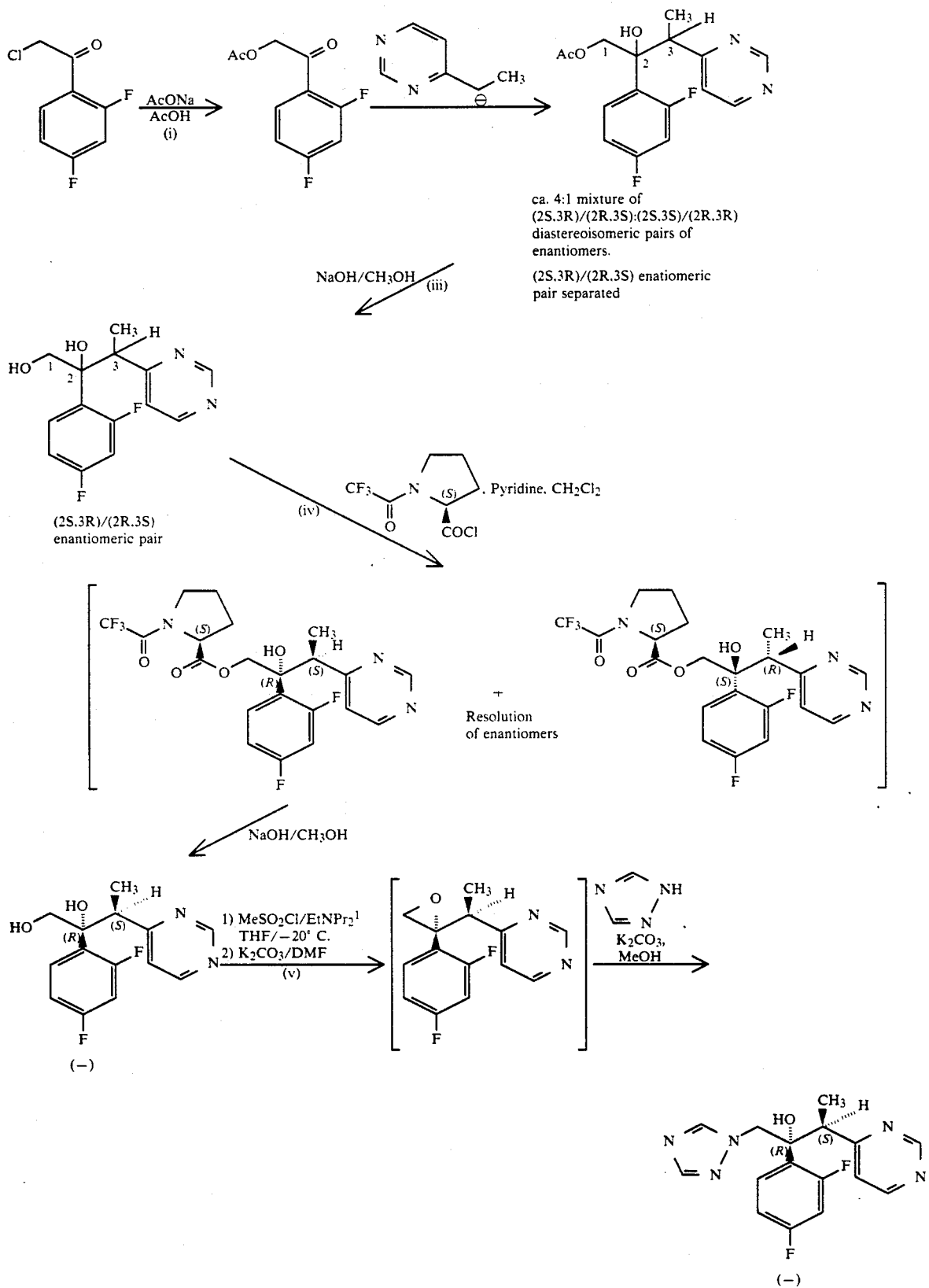

acid (50 ml) was heated under reflux for 4 hours and then evaporated. The residue was partitioned between ethyl acetate and water. The organic layer was separated, washed with sodium bicarbonate solution and dried (Na$_2$SO$_4$). Evaporation of the solvent gave an oil which was triturated with hexane. The resulting solid was filtered off, washed with hexane and dried to give the title compound, (16.2 g), m.p. 54°–56°.

(ii) (±)-(2R,3S) and (2S,3R)-1-Acetoxy-2-(2,4-difluorophenyl)-3-(pyrimidin-4-yl)butan-2-ol A solution of diisopropylamine (30.3 g) in dry tetrahydrofuran (400 ml) was treated successively with n-butyllithium (188 ml of a 1.6M solution in hexane) followed by 4-ethylpyrimidine (32.4 g) according to the method of Example 3. A solution of the product of part (i) (64.0 g) in dry tetrahydrofuran (400 ml) was added with stirring over 0.58 hour at −40° to −50°. Acetic acid (30 ml) was then added and the solution was allowed to reach room temperature. Ether (1000 ml) and water (1000 ml) were added and the mixture was shaken. The organic layer was separated, washed with brine and dried (MgSO$_4$). The solvent was evaporated and the residue was chromatographed on silica gel. Elution with ether/hexane (1:4) gave starting ketone initially. Further elution with ether/hexane (1:1), gradually decreasing the proportion of hexane until neat ether was being used, gave a semi-solid consisting of a (±)-enantiomeric mixture of the title compounds together with the (2R,3R)- and (2S,3S)-diastereoisomeric pair of enantiomers. Ether was added until a clear solution was obtained and then hexane (20% by volume) was added. The mixture was cooled and the resulting solid was filtered off, washed with hexane and dried to give the (±)-enantiomeric mixture of the title compounds, (23.3 g), m.p. 102°–103.5°.

Analysis %: Found: C,59.68; H,5.09; N,8.55; C$_{16}$H$_{16}$F$_2$N$_2$O$_3$ requires: C,59.62; H,5.00; N,8.69.

(iii) (±)-(2R,3S) and (2S,3R)-2-(2,4-Difluorophenyl)-3-(pyrimidin-4-yl)butan-1,2-diol 2N Sodium hydroxide solution (40 ml) was added with stirring over 0.25 hour to a solution of the product of part (ii) (23.3 g) in methanol (80 ml) and stirring was continued for a further 0.25 hour. Water (150 ml) was added and the mixture was cooled. The solid was filtered off, washed with water and dried to give the title compounds, (17.4 g), m.p. 148.5°–150.5°.

Analysis %: Found: C,59.80; H,5.09; N,10.12; C$_{14}$H$_{14}$F$_2$N$_2$O$_2$ requires: C,60.00; H,5.04; N,10.00.

(iv) (−)-(2R,3S)-2-(2,4-Difluorophenyl)-3-(pyrimidin-4-yl)butan-1,2-diol (S)-N-(Trifluoroacetyl)prolyl chloride (72 ml of 1.0M solution in dichloromethane) was added dropwise over 0.5 hour to an ice-cooled solution of the product of part (iii) (16.7 g) and pyridine (8.7 ml) in dry dichloromethane (50 ml). The solution was stirred for 0.5 hour and then the dichloromethane was evaporated. Ethyl acetate and water were added and the mixture was acidified to pH3 with 2N hydrochloric acid. The organic layer was separated, washed successively with 0.1N hydrochloric acid and water, then dried (Na$_2$SO$_4$). The solvent was evaporated and the residue was chromatographed on silica gel. The column was eluted with hexane/ether/diethylamine (65:30:5) and the initial product-containing fractions were combined and evaporated. The residue was crystallised from diisopropyl ether to give the (S)-N-(trifluoroacetyl)prolyl ester of the title (2R,3S)-enantiomer, (4.78 g), m.p. 91°–92.5°.

Further elution of the column gave fractions containing a mixture of both the (2R,3S)- and (2S,3R)-enantiomers as their (S)-N-(trifluoroacetyl)prolyl esters. The appropriate fractions were combined and evaporated, and this residue was combined with the residue obtained by evaporation of the mother liquors from the crystallisation above. The combined mixture was dissolved in a little diisopropyl ether, the solution was seeded with a crystal of the pure (2R,3S)-product and cooled for 4 hours. Filtration afforded a further 1.90 g of the pure (2R,3S)-enantiomer as the (S)-N-(trifluoroacetyl)prolyl ester.

The absolute stereochemistry of this product was confirmed by X-ray crystallography.

The above ester of the title compound (6.0 g) was dissolved in methanol (28 ml) and 2N sodium hydroxide solution (14 ml) was added. After 0.25 hour, water (100 ml) was added and the mixture was cooled in ice for 1 hour. The solid was filtered off, washed with water and dried to give the title compound, (2.50 g), m.p. 147.5°–148.5°.

Analysis %: Found: C,59.94; H,5.16; N,9.97; C$_{14}$H$_{14}$F$_2$N$_2$O$_2$ requires: C,60.00; H,5.04; N,10.00.

(v) (−)-(2R,3S)-2-(2,4-Difluorophenyl)-3-(pyrimidin-4-yl)-1-(1H-1,2,4-triazol-1-yl)butan-2-ol Methanesulphonyl chloride (1.15 g) was added to a stirred solution of the product of part (iv) (2.35 g) and diisopropylethylamine (2.38 g) in dry tetrahydrofuran (30 ml) at −10° to −20° under an atmosphere of dry nitrogen. The solution was stirred at the same temperature for 1 hour and then anhydrous potassium carbonate (7.0 g) and dry N,N-dimethylformamide (25 ml) were added. The mixture was stirred at room temperature for 1.5 hours and then partitioned between water and ether. The organic layer was separated, washed with water and dried (Na$_2$SO$_4$). Evaporation of the solvent gave an oil which was immediately dissolved in methanol (50 ml). 1H-1,2,4-Triazole (6.0 g) and anhydrous potassium carbonate (6.0 g) were added and the mixture was heated at 60° with stirring for 40 hours, then evaporated. The residue was partitioned between ethyl acetate/ether (1:1) and water, the organic layer was separated and washed with water, then dried (Na$_2$SO$_4$). The solvent was evaporated and the residue was chromatographed on silica gel. Initial elution with ethyl acetate gave impurity-containing fractions, and subsequent further elution with ethyl acetate/methanol (20:1) gave, after combination and evaporation of appropriate fractions, the title compound, (0.87 g), m.p. 55°–58°, [α]25/D −65.1° (0.55% in methanol).

N.M.R. (300 MHz): δ(CDCl$_3$)=1.13 (d, 3H, J=7.12 Hz, CH$_3$), 3.68 (q, 1H, J=7.12 Hz, CHCH$_3$), 4.16 and 4.78 (d, 1H, J=14.1 Hz, CH$_2$), 6.60 (s, 1H, OH), 6.82 (m, 2H, H$_{arom}$), 7.44 (d, 1H, J=5.0 Hz, pyrimidine H-5), 7.57 (m, 1H, H$_{arom}$), 7.61 and 7.96 (s, 1H, triazole H), 8.77 (d, 1H, J=5.0 Hz, pyrimidine H-6), 9.17 (s, 1H, pyrimidine H-2) p.p.m.

It is believed that where diastereoisomeric pair B is isolated in the above Examples, that it is a mixture of the (2R,3S) and (2S,3R) diastereoisomers.

We claim:

1. A pharmaceutical composition for treating a fungal infection in a human which comprises an antifungel effective amount of a compound of the formula

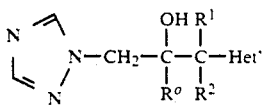

or a pharmaceutically acceptable acid addition salt thereof, wherein $R^0$ is mono- or disubstituted phenyl wherein said substituent is each chloro, fluoro, bromo or trifluoromethyl, $R^1$ is alkyl having one to four carbon atoms; $R^2$ is hydrogen or alkyl having one to four carbon atoms; and Het' is pyridinyl, pyridazinyl, pyrimidinyl, pyrazinyl or triazinyl or substituted pyridinyl, pyridazinyl, pyrimidinyl, pyrazinyl or triazinyl wherein said substituent is alkyl having one to four carbon atoms, alkoxy having one to four carbon atoms, fluoro, chloro, bromo, trifluoromethyl, cyano, nitro, amino, alkanoylamino having one to four carbon atoms or alkoxycarbonylamino having two to five carbon atoms together with a pharmaceutically acceptable carrier.

2. A method of treating a fungal infection in a human which comprises administering to said human an antifungal effective amount of a compound of the formula

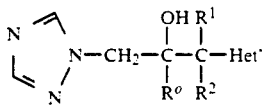

or a pharmaceutically acceptable acid addition salt thereof, wherein $R^0$ is mono- or disubstituted phenyl wherein said substituent is each chloro, fluoro, bromo or trifluoromethyl, $R^1$ is alkyl having one to four carbon atoms; $R^2$ is hydrogen or alkyl having one to four carbon atoms; and Het' is pyridinyl, pyridazinyl, pyrimidinyl, pyrazinyl or triazinyl or substituted pyridinyl, pyridazinyl, pyrimidinyl, pyrazinyl or triazinyl wherein said substituent is alkyl having one to four carbon atoms, alkoxy having one to four carbon atoms, fluoro, chloro, bromo, trifluoromethyl, cyano, nitro, amino, alkanoylamino having one to four carbon atoms or alkoxycarbonylamino having two to five carbon atoms.

3. A method of claim 2, wherein $R^0$ is difluorophenyl, dichlorophenyl, fluorophenyl or chlorophenyl; $R^1$ is alkyl having one to four carbon atoms; $R^2$ is hydrogen or alkyl having one to four carbon atoms; and Het' is pyridinyl, pyridazinyl, pyrimidinyl, pyrazinyl or triazinyl, optionally substituted with a cyano group.

4. The method of claim 3, wherein $R^1$ is methyl and $R^2$ is hydrogen.

5. The method of claim 4, wherein $R^0$ is 2-chlorophenyl, 2-fluorophenyl, 2,4-dichlorophenyl or 2,4-difluorophenyl and Het' is 2-pyridinyl, 4-pyridinyl or 4-pyrimidinyl.

6. The method of claim 5, wherein the compound is selected from the group consisting of 2-(2,4-difluorophenyl)-3-(pyridin-2-yl)-1-(1H-1,2,4-triazol-1-yl)butan-2-ol, 2-(2,4-difluorophenyl)-3-(pyridin-4-yl)-1-(1H-1,2,4-triazol-1-yl)butan-2-ol and 2-(2,4-difluorophenyl)-3-(pyrimidin-4-yl)-1-(1H,1,2,4-triazol-1-yl)butan-2-ol.

7. A method of claim 6, wherein the compound is 2-(2,4-difluorophenyl)-3-(pyrimidin-4-yl)-1-(1H,1,2,4-triazol-1-yl)butan-2-ol.

8. A method of claim 6, wherein the fungal infection is caused by the Aspergillus sp fungi.

9. A method of claim 8, wherein the Aspergillus sp fungi is *Aspergillus fumigatus*.

* * * * *